United States Patent
Sinko et al.

(10) Patent No.: US 9,517,201 B2
(45) Date of Patent: Dec. 13, 2016

(54) NANOCARRIER AND NANOGEL COMPOSITIONS

(75) Inventors: Patrick J. Sinko, Lebanon, NJ (US); Stanley Stein, East Brunswick, NJ (US); Hilliard Kutscher, Stockton, NJ (US); Manjeet Deshmukh, Highland Park, NJ (US); Anupa Menjoge, Hayward, GA (US); Yashveer Singh, Highland Park, NJ (US); Simi Gunaseelan, North Brunswick, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 766 days.

(21) Appl. No.: 12/936,392

(22) PCT Filed: Apr. 6, 2009

(86) PCT No.: PCT/US2009/002164
§ 371 (c)(1), (2), (4) Date: Dec. 22, 2010

(87) PCT Pub. No.: WO2009/123768
PCT Pub. Date: Oct. 8, 2009

(65) Prior Publication Data
US 2011/0117024 A1    May 19, 2011

Related U.S. Application Data

(60) Provisional application No. 61/042,577, filed on Apr. 4, 2008.

(51) Int. Cl.
| | | |
|---|---|---|
| *A61K 9/14* | (2006.01) |
| *A61K 9/06* | (2006.01) |
| *A61K 9/10* | (2006.01) |
| *A61K 9/16* | (2006.01) |
| *A61K 31/704* | (2006.01) |
| *A61K 47/10* | (2006.01) |
| *A61K 49/00* | (2006.01) |
| *A61K 9/48* | (2006.01) |
| *A61K 9/51* | (2006.01) |
| *A61K 47/48* | (2006.01) |

(52) U.S. Cl.
CPC . *A61K 9/06* (2013.01); *A61K 9/10* (2013.01); *A61K 9/1641* (2013.01); *A61K 31/704* (2013.01); *A61K 47/10* (2013.01); *A61K 47/48215* (2013.01); *A61K 47/48246* (2013.01); *A61K 49/003* (2013.01); *A61K 49/0043* (2013.01); *A61K 49/0054* (2013.01); *A61K 9/14* (2013.01); *A61K 9/48* (2013.01); *A61K 9/51* (2013.01); *A61K 47/48007* (2013.01); *A61K 47/48169* (2013.01); *A61K 47/48869* (2013.01); *Y10T 428/2982* (2015.01)

(58) Field of Classification Search
None
See application file for complete search history.

(56) References Cited

U.S. PATENT DOCUMENTS

| | | |
|---|---|---|
| 6,521,431 B1 | 2/2003 | Kiser et al. |
| 6,696,089 B2 | 2/2004 | Kabanov et al. |
| 7,202,330 B2 | 4/2007 | Dejong et al. |
| 2003/0124742 A1* | 7/2003 | Prakash .................. 436/518 |
| 2004/0161403 A1* | 8/2004 | Zhao et al. ............. 424/78.19 |
| 2004/0228831 A1* | 11/2004 | Belinka et al. ........ 424/78.27 |
| 2005/0118252 A1 | 6/2005 | Bae et al. |
| 2006/0127386 A1 | 6/2006 | Muzykantov et al. |
| 2006/0204582 A1 | 9/2006 | Stein et al. |

* cited by examiner

Primary Examiner — James Rogers
(74) Attorney, Agent, or Firm — Fox Rothschild LLP

(57) ABSTRACT

Novel classes of multi-arm polyalkylene oxide-based materials including PEG nanocarriers, nanogel particles, and aggregated nanogel particles are disclosed. These classes of compositions may be associated with therapeutic agents and targeting moieties, or visibility enhancing agents, and may have a modified surface structure. In some embodiments the PEG-based materials can be made to provide relatively high drug loads with improved solubility and targeted delivery.

7 Claims, 14 Drawing Sheets

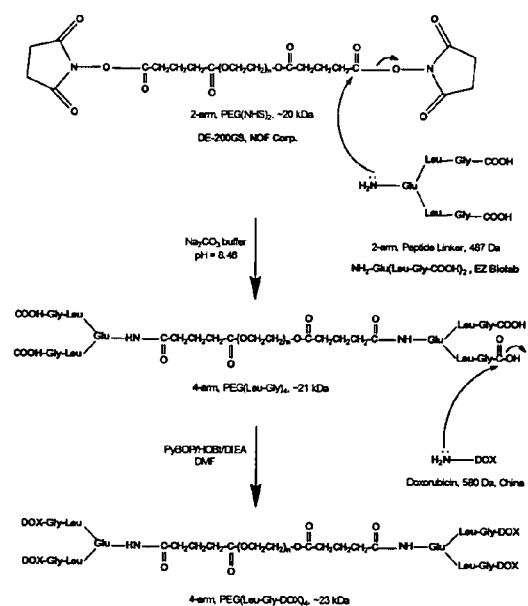
Figure 1. Preparation of PEGylated Dox nanocarrier {PEG$_{20kDa}$[Glu(Leu-Gly-Dox)$_2$]$_2$ (4 copy Dox)}.

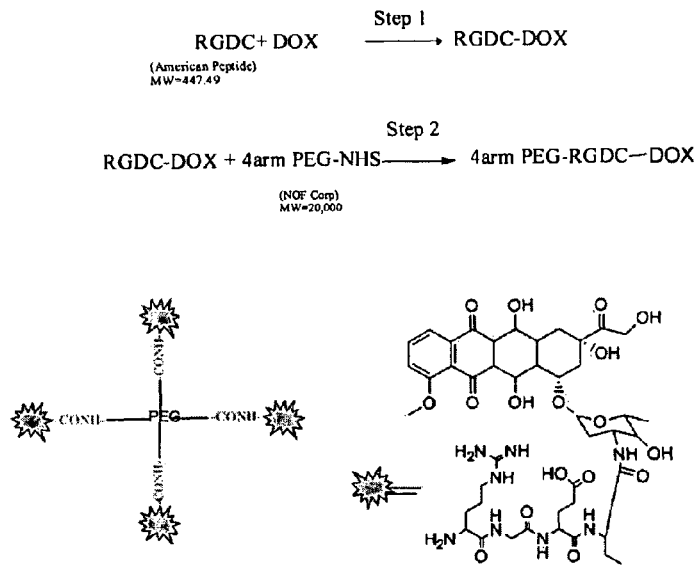
Figure 2. Preparation of PEGylated Dox nanocarrier {PEG$_{20kDa}$(RGDC-Dox)$_4$ (4 copy Dox)}.
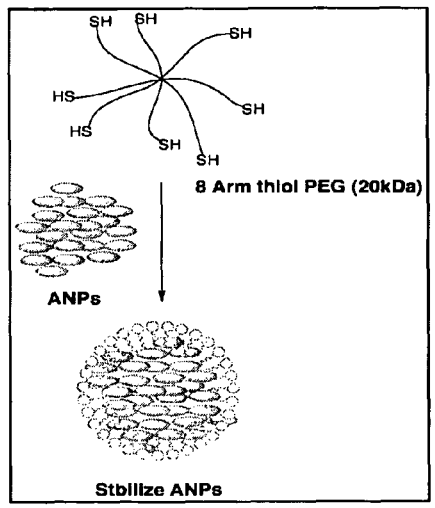
Figure 3. Synthesis of stabilized aggregated nano particles (ANPs).

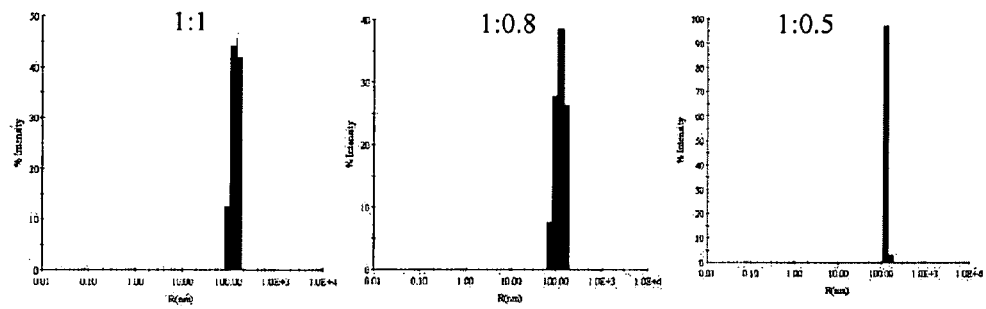
Figure 4. NPs size determination using Dynamic Light Scattering (DLS).
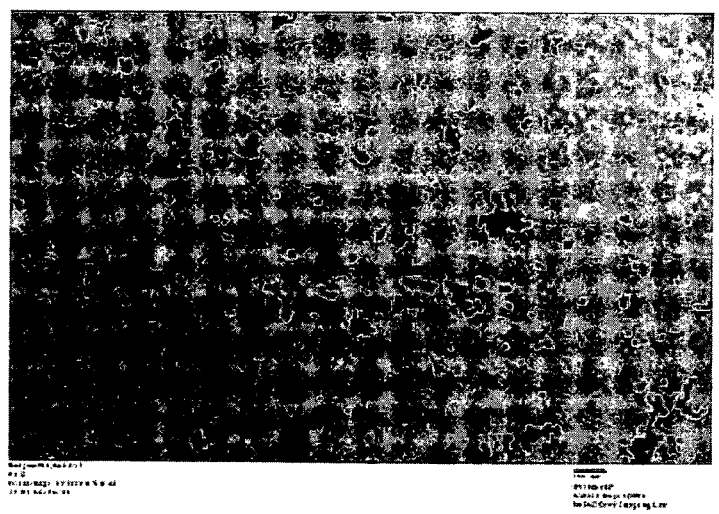
Figure 5: Morphology and size of NPs using Transmission Electron Microscope (TEM), Particle size: 20-100 nm.

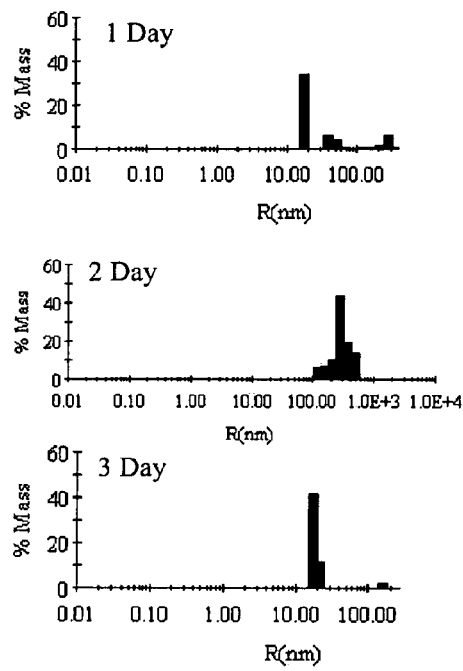
Figure 6. NPs size determination using Dynamic Light Scattering (DLS) spectrophotometer.
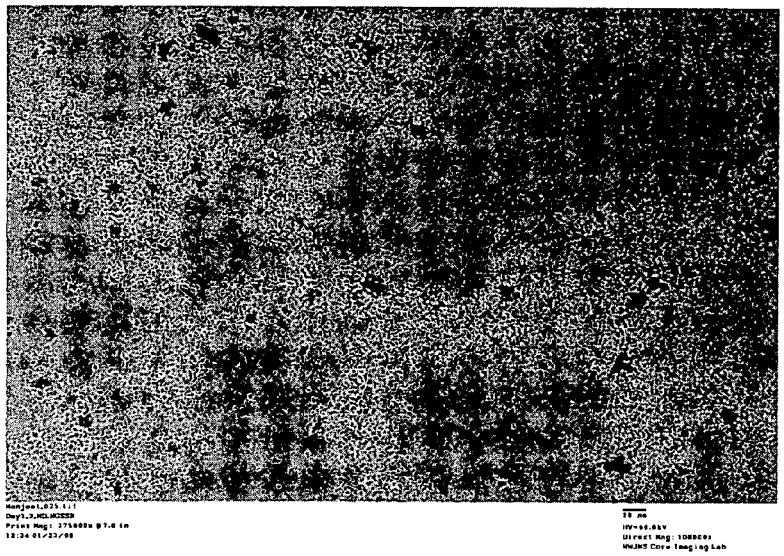
Figure 7. Morphology and size of NPs using Transmission Electron Microscopy (TEM), particle size: 20-40 nm.

Figure 8. Morphology and size of NPs using Transmission Electron Microscopy (TEM), particle size: 20-300 nm.
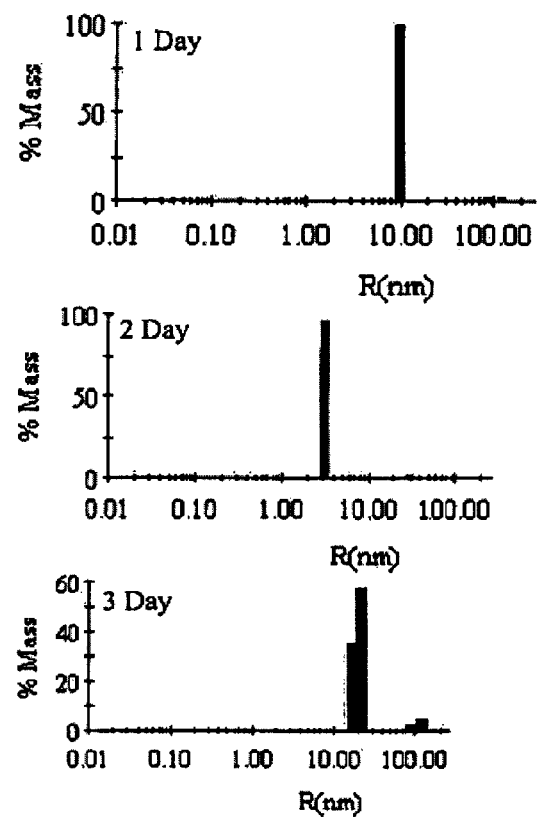
Figure 9. NPs size determination using Dyanamic Light Scattering (DLS) spectrophotometer. NPs preparation using surfactant and stirring time of 1 day, 2 days, and 3 days.

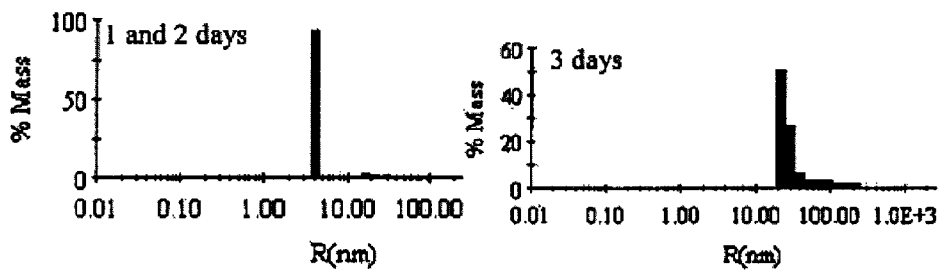
Figure 10. NPs size determination using Dyanamic Light Scattering (DLS) spectrophotometer. NPs were prepared using surfactant, sonication and stirring time of 1 day, 2 days, and 3 days.
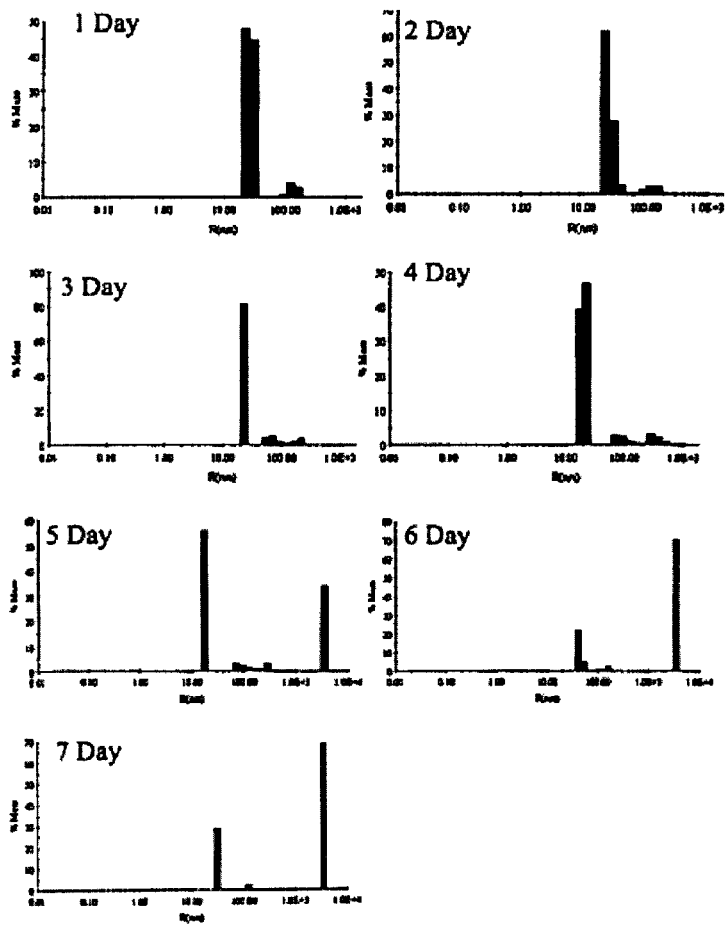
Figure 11. NPs size determination using Dynamic Light Scattering (DLS) spectrophotometer. Effects of surfactant, sonication and stirring time on ANPs size is shown.

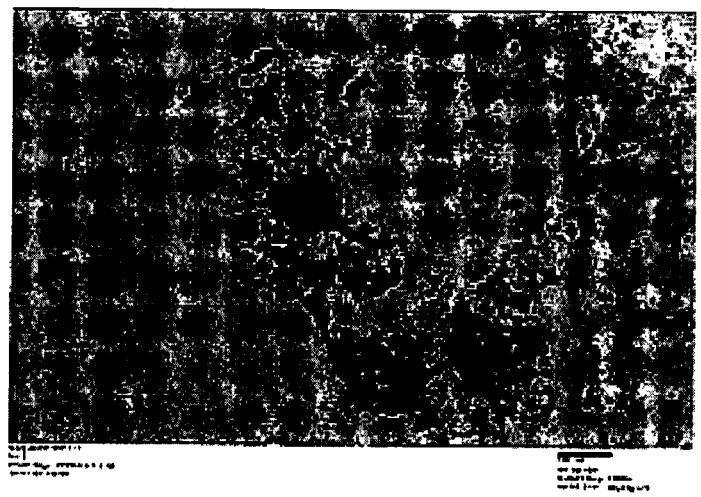
Figure 12. Morphology and size of ANPs (~ 10 micron) using Transmission Electron Microscopy (TEM).

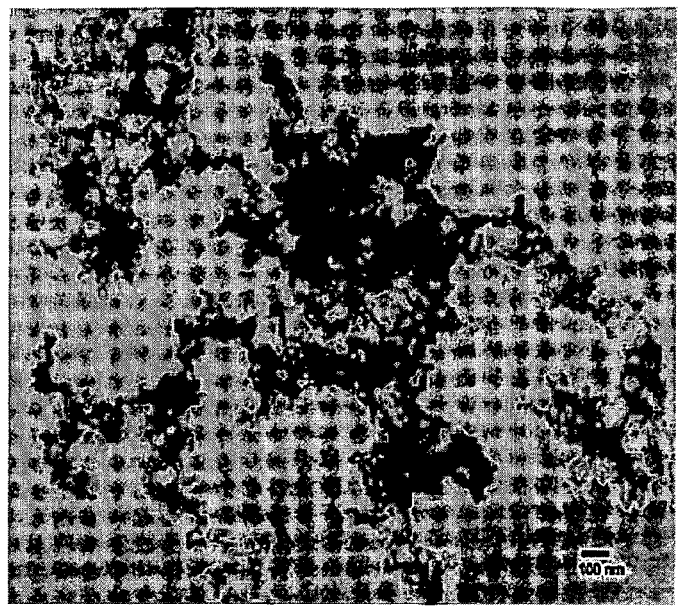
Figure 13. Morphology and size of ANPs (~ 18 micron) using Transmission Electron Microscopy (TEM).
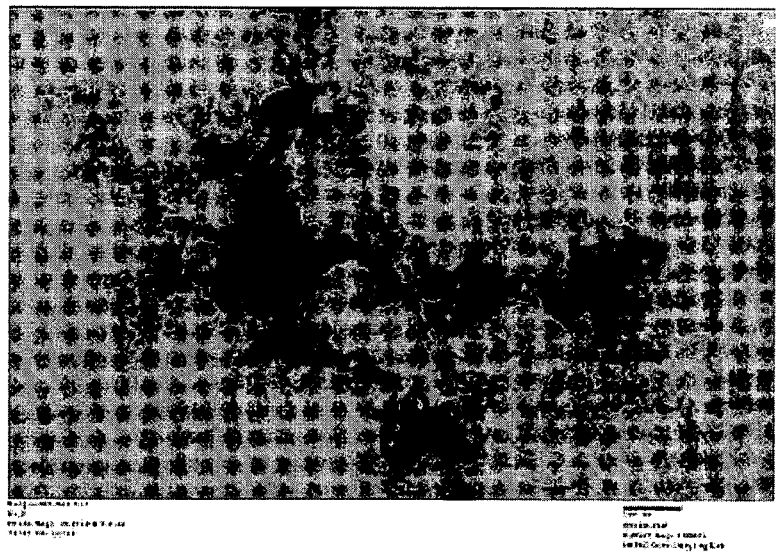
Figure 14. Morphology and size of ANPs (~24 micron) using Transmission Electron Microscopy (TEM).

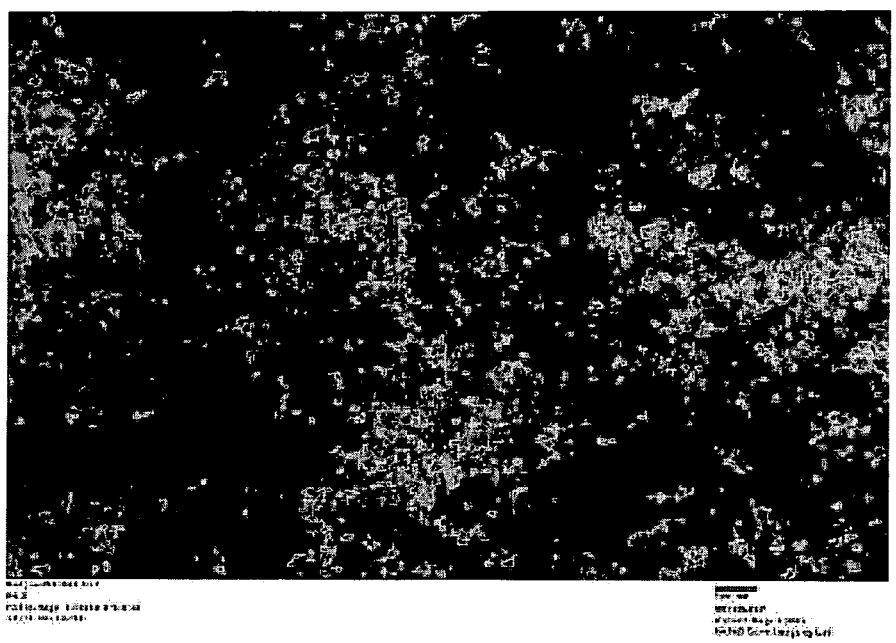
Figure 15. Morphology and size of ANPs (~ 24 micron) using Transmission Electron Microscopy (TEM).

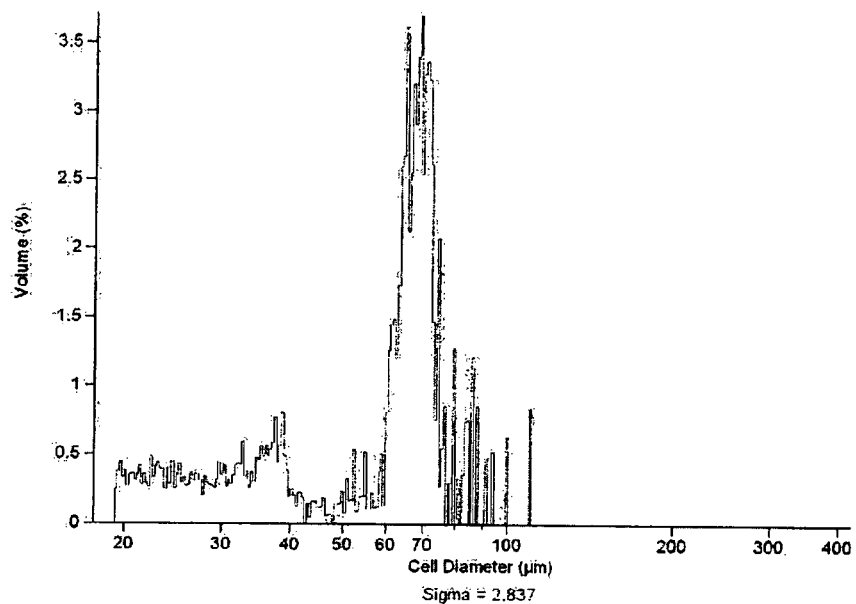
Figure 16. Size determination of sonicated ANPs using coulter counter.
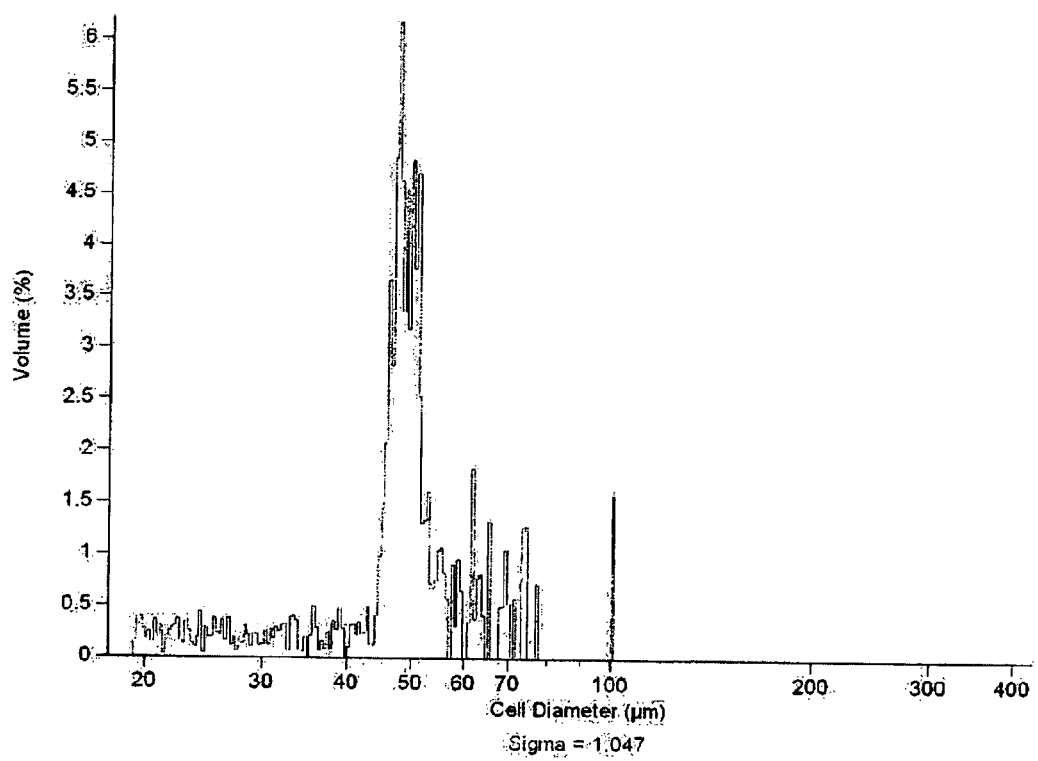
Figure 17. Size determination of sonicated ANPs using coulter counter.

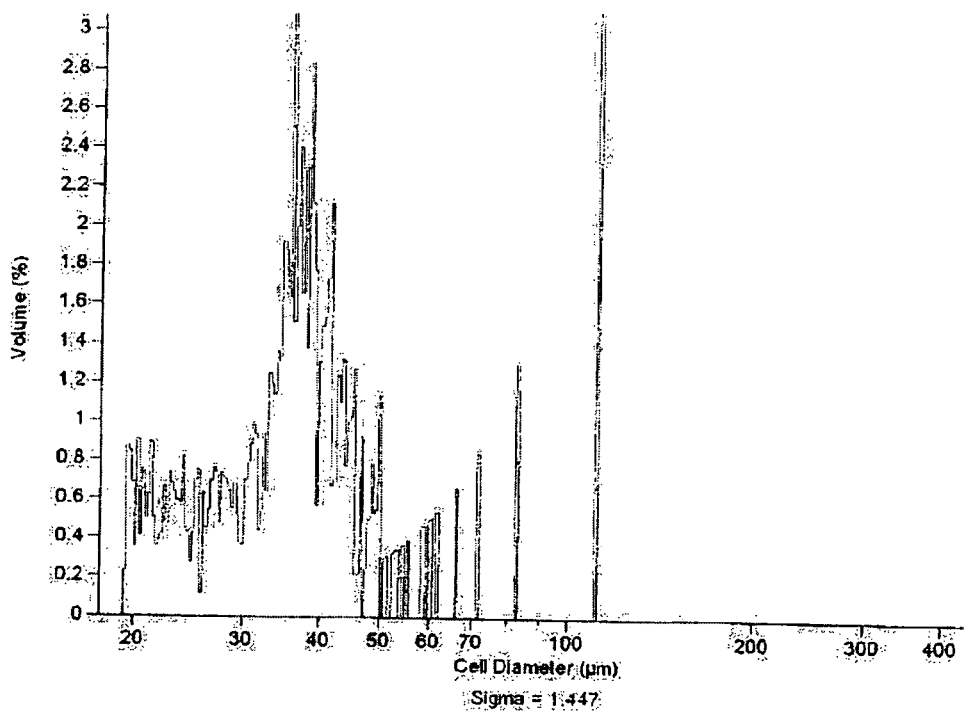
Figure 18. Size determination of sonicated ANPs using coulter counter.
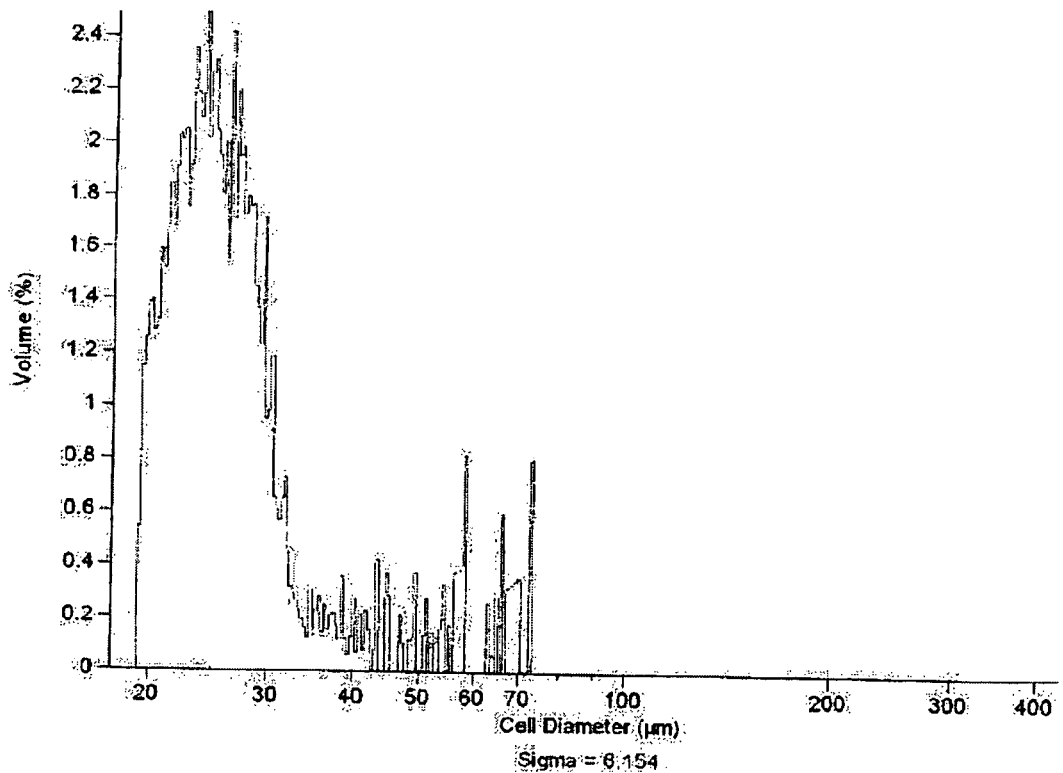
Figure 19. Size determination of sonicated ANPs using coulter counter.

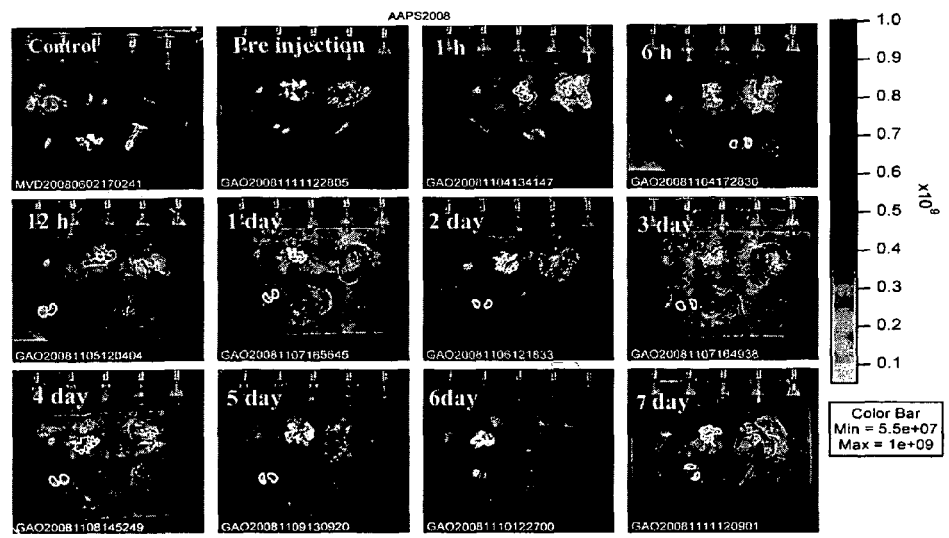
Figure 20. Biodistribution studies of DYE-ANPs (particle size: 50-60 µm) in rats using IVIS 100 optical imager.
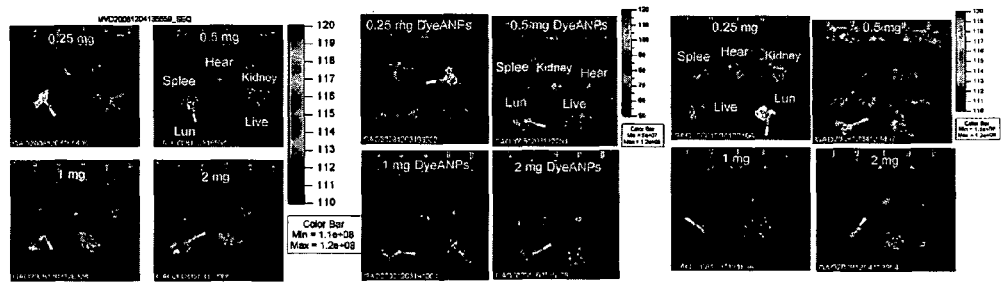
Figure 21. Biodistribution studies of DYE-ANPs (particle size: 30-50 µm) in rats using IVIS 100 optical imager.

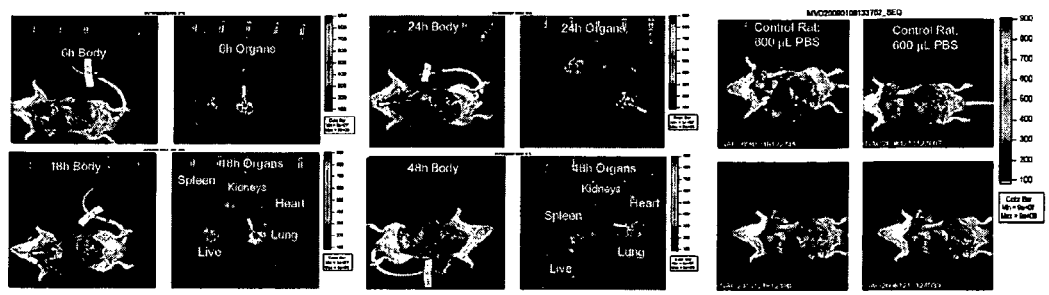
Figure 22. Biodistribution studies of DYE-ANPs (particle size: 10-20 μm) in rats using IVIS 100 optical imager.
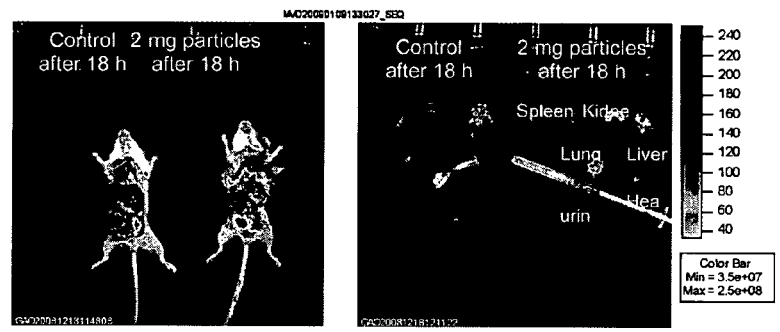
Figure 23. Biodistribution studies of DYE-ANPs (particle size: 10-20 μm) in mice using IVIS 100 optical imager.

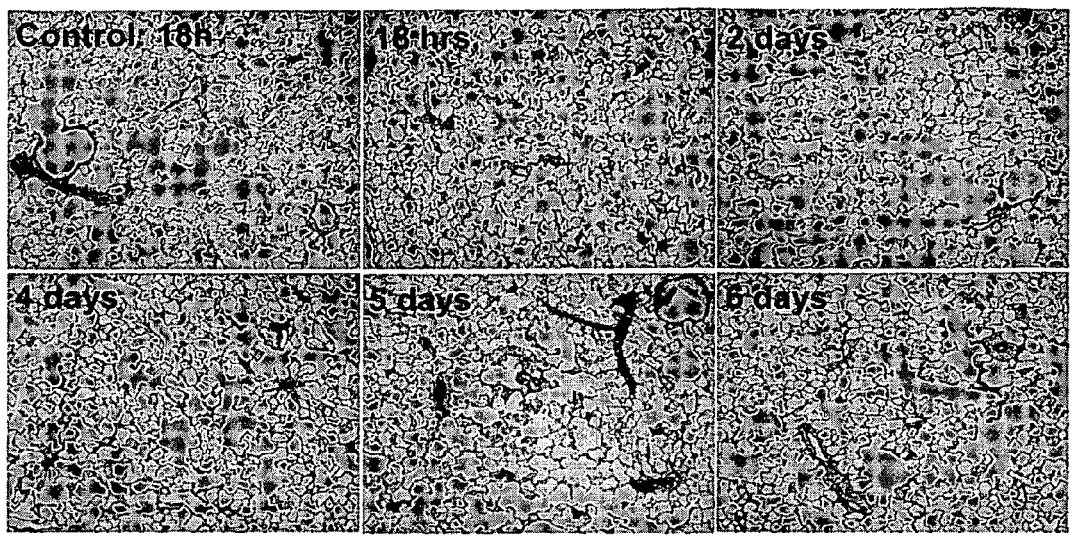
Figure 24. Lung histology following ANP injection (20 μm). Magnification 100x.

SEQUENCE LISTING

```
<160> NUMBER OF SEQ ID NOS: 8

<210> SEQ ID NO 1
<211> LENGTH: 5
<212> TYPE: PRT
<213> ORGANISM: Artificial Sequence
<220> FEATURE:
<223> OTHER INFORMATION: Synthetic

<400> SEQUENCE: 1

Glu Leu Gly Leu Gly
1               5
```

```
<210> SEQ ID NO 2
<211> LENGTH: 4
<212> TYPE: PRT
<213> ORGANISM: Artificial Sequence
<220> FEATURE:
<223> OTHER INFORMATION: Synthetic

<400> SEQUENCE: 2

Arg Gly Asp Cys
1

<210> SEQ ID NO 3
<211> LENGTH: 5
<212> TYPE: PRT
<213> ORGANISM: Artificial Sequence
<220> FEATURE:
<223> OTHER INFORMATION: Synthetic

<400> SEQUENCE: 3

Gly Arg Gly Asp Ser
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic

<400> SEQUENCE: 4

Gly Arg Gly Asp Ser Pro
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic

<400> SEQUENCE: 5

Arg Gly Asp Tyr Lys
1               5

<210> SEQ ID NO 6
<211> LENGTH: 11
<212> TYPE: PRT
<213> ORGANISM: Artificial Sequence
<220> FEATURE:
<223> OTHER INFORMATION: Synthetic DV3 Peptide

<400> SEQUENCE: 6

Leu Gly Ala Ser Trp His Arg Pro Asp Lys Cys
1               5                   10

<210> SEQ ID NO 7
<211> LENGTH: 9
<212> TYPE: PRT
<213> ORGANISM: Artificial Sequence
<220> FEATURE:
<223> OTHER INFORMATION: Synthetic LYP peptide

<400> SEQUENCE: 7

Cys Gly Asn Lys Arg Thr Arg Gly Cys
1               5

<210> SEQ ID NO 8
```

```
<211> LENGTH: 14
<212> TYPE: PRT
<213> ORGANISM: Artificial Sequence
<220> FEATURE:
<223> OTHER INFORMATION: Synthetic membrane binding domain of IGFBP3

<400> SEQUENCE: 8

Gln Cys Arg Pro Ser Lys Gly Arg Lys Arg Gly Phe Cys Trp
1               5                   10
```

NANOCARRIER AND NANOGEL COMPOSITIONS

CROSS-REFERENCE TO RELATED APPLICATIONS

This application is a National Stage filing under 35 U.S.C. §371 of International Application Serial No. PCT/US09/02164 which claims priority to U.S. Provisional Patent Application No. 61/042,577 filed on Apr. 4, 2008, both of which are hereby incorporated by reference in their entirety.

BACKGROUND OF THE INVENTION

1. Field of the Invention

Embodiments of the present invention relate to compositions of polyalkylene oxide polymers, as well as methods of making and using the polymers and kits for their use. More particularly, embodiments relate to compositions comprising functionalized polyethylene glycol (PEG) in new and useful configurations as nanocarriers, nanogel particles and aggregated nanogel particles.

2. Description of the Related Art

PEG conjugation has been widely used to improve the water solubility and systemic persistence of drugs such as interferon. Typically, one PEG is conjugated to one interferon molecule resulting in a therapeutically effective drug product. This only works well for highly potent drugs since the mass of polymeric carrier in a drug product becomes prohibitively large for high dose drugs. Further, in order to improve biological properties, other agents such as cell adhesion peptides have been linked to the same types of drugs. For example, Doxorubicin has been linked to a bicyclic RGD peptide, however, this resulted in the loss of aqueous solubility (F. H. de Groot, H. J. Broxterman, H. P. H. M. Adams, A. van Vliet, G. I. Tesser, Y. W. Elderkamp, A. J. Schraa, R. J. Kok, G. Molema, H. M. Pinedo, H. W. Scheeren, *Molecular Cancer Therapeutics*, 2002, 1, 901-911). Also, previous attempts at increasing drug loading on polymeric carriers have only partially succeeded. For example, it was demonstrated that water solubility was lost when more than three copies of campthothecin were attached to PEG (J. J. Khandare, P. Chandna, Y. Wang, V. P. Pozharov, T. Minko, *Journal of Pharm. Exper. Ther.*, 2006, 317, 929-937). Further, Andersson et al. demonstrated that a high molecular weight polymeric carrier capable of increasing the loading of doxorubicin could be synthesized. However, the size of the carrier was very large and the authors concluded "it became clear from the outset . . . that they do not possess the desired solubility . . . even after prolonged sonication" (L. Andersson, J. Davies, R. Duncan, P. Ferruti, J. Ford, S. Kneller, R. Mendichi, G. Pasut, O. Schiavon, C. Summerford, A. Tirk, F. Veronese, V. Vincenzi, and G. Wu. *Biomacromolecules*, 2005, 6 (2), 914-926). Desai, et al. have reported in U.S. Pat. No. 5,648,506 attaching taxol to 8-arm PEG through urethane and ester linkages, but do not describe thioether or disulfide linkages, nanocarriers, nanogel particles, aggregated nanogel particles, gelation that can occur in vivo, gelation with relatively nontoxic materials, crosslinking of PEG with the PEG not being part of a PEG/nonPEG copolymer, or any aspect of sulfur chemistry. Therefore, although it is desirable to have more than one copy of a drug or agent on a single nanocarrier having acceptable aqueous solubility, and biological characteristics, it has not been achieved to date.

SUMMARY OF THE INVENTION

In one embodiment, the invention is directed to a nanocarrier, comprising an agent coupled to a multi-arm polyalkylene oxide, wherein the molar ratio of agent to multi-arm polyalkylene oxide is greater than about 1:1 and the nanocarrier exhibits an aqueous solubility of at least about 0.1 mg/ml. In certain embodiments, the nanocarrier has a molar ratio greater than about 1.2:1. In certain embodiments, the nanocarrier has a molar ratio greater than about 1.5:1. In certain embodiments, the nanocarrier has a molar ratio greater than about 1.8:1. In certain embodiments, the nanocarrier has a molar ratio greater than about 2.1:1.

In accordance with the above embodiments, the invention is also directed to a nanocarrier that has an aqueous solubility is at least about 10 mg/ml. In certain other embodiments, the nanocarrier aqueous solubility is at least about 33 mg/ml. In certain embodiments, the nanocarrier aqueous solubility is at least about 100 mg/ml. In certain embodiments, the nanocarrier aqueous solubility is at least about 1000 mg/ml.

In accordance with the above embodiments, the invention is also directed to a nanocarrier wherein the multi-arm polyalkylene oxide is PEG. In certain embodiments, the PEG is a 4- or 8-arm PEG. In certain embodiments, the PEG is functionalized with terminal SH groups.

In accordance with the above embodiments, the invention comprises an agent selected from the group consisting of anti-inflammatory agents. In certain embodiments, the agent is selected from the group consisting of non-steroidal anti-inflammatory drugs (NSAID) and NSAID analogs, indomethacin, sancycline and sancycline analogs, olvanil and olvanil analogs, retro-olvanil and retro-olvanil analogs, olvanil carbamate, NSAID-ache (NSAID complexed with acetylcholine esterase inhibitor), budesonide and budesonide analogs, methylprenisolone and methylprenisolone analogs and dexamethasone and dexamethasone analogs. In certain embodiments, the anti-inflammatory agent (Y) is coupled to the PEG (X) by a linker (X-AA-Y) where AA can be —CH2-CH2-, —CH2-CH2-CH2-, —CH2-CH2-, —CH2-CH2-CONH—CH2-COOH, —CH2-CH2-CONH—CH[(CH2)2-COOH]—COOH, —CH2-CH2-CONH—CH[(CH2)4-NH2]—COOH, etc. In certain other embodiments, the agent is doxorubicin. In certain other embodiments the agent is coupled to the PEG by a linking group selected from the group consisting of peptide linkers, enzyme sensitive peptide linkers/linkers, self-immolative linkers, acid sensitive linkers, multifunctional organic linking agents, bifunctional inorganic crosslinking agents, Leu-Gly, Glu(Leu-Gly)2, Arg-Gly-Asp-Cys, Gly-Arg-Gly-Asp-Ser, Gly-Arg-Gly-Asp-Ser-Pro, cyclic Arg-Gly-Asp-Tyr-Lys, or any peptide with Arg-Gly-Asp. In certain embodiments, the doxorubicin is coupled to the PEG by a linker selected from the group consisting of Leu-Gly, Glu(Leu-Gly)2, Arg-Gly-Asp-Cys, Gly-Arg-Gly-Asp-Ser, Gly-Arg-Gly-Asp-Ser-Pro, cyclic Arg-Gly-Asp-Tyr-Lys, or any peptide with Arg-Gly-Asp. In certain embodiments, the agent is selected from the group consisting of HIV Protease Inhibitors: saquinavir mesylate, amprenavir, ritonavir, indinavir, nelfinavir mesylate, tipranavir, darunavir and atazanavir sulfate. In certain other embodiments, the agent is coupled to the PEG by linking group selected from the group consisting of peptidic backbones represented as: $CH_3CO—(X—Z—Z)_x—(Y—Z—Z)_y—CONH_2$, where X=Lys, Glu, Asp or diaminobutyric acid; Y=Cys, homocysteine or 1-amino-2-methyl-2-propanethiol; Z=β-Ala, Gly, Ala, or GABA (gamma-amino butyric acid); x and y are interchangeable; x is between 1 to 4; y is between 1 to 4; minimum no. of Z-spacer on the peptide backbone=2. In certain embodiments, the agent is selected from the group of imaging agents including coloring dyes like FD and C dyes, or visible/near infrared fluorescence dyes like fluorescein, methylene blue, rhodamine, dansyl, Alexa, cyanine dyes, Hilyte, indocyanine green etc. In certain other embodiments, the agent is directly or indirectly (by any standard linking group) coupled to the PEG.

In accordance with the above embodiments, the invention further comprises one or more copies of a targeting moiety. In certain embodiments, the targeting moiety is a peptide. In certain other embodiments, the peptide is an RGD peptide. In certain other embodiments, the peptide is a DV3 (LGAS-WHRPDKC) peptide. In certain other embodiments, the peptide is a LYP peptide (CGNKRTRGC). In certain other embodiments, the peptide is a membrane binding domain of IGFBP3 (QCRPSKGRKRGFCW). In certain other embodiments, the peptide is fMLF. In certain other embodiments, the targeting agent is mannose. In certain other embodiments, the targeting agent is transferrin ligand. In certain other embodiments, the targeting agent is monoclonal antibodies.

The invention is also directed to a nanogel particle comprising a multi-arm polyalkylene oxide crosslinked via a bond such as a disulfide and/or thioether bonds, wherein the nanogel particle has a mean particle size of greater than about 1 nm. In certain embodiments, the nanogel mean particle size is greater that about 5 nm. In certain other embodiments, the mean particle size is greater that about 10 nm. In certain other embodiments, the mean particle size is greater that about 100 nm.

In accordance with any of the above embodiments, the invention is also directed to a nanogel particle wherein the multi-arm polyalkylene oxide is PEG. In certain other embodiments, the PEG is a 4- or 8-arm PEG. In certain other embodiments, the PEG is functionalized with terminal SH groups.

In accordance with any of the above embodiments, the invention further comprises an agent. In certain embodiments, the agent is selected from the group consisting of anti-inflammatory drugs including: non-steroidal anti-inflammatory drugs (NSAID) and NSAID analogs, indomethacin, sancycline and sancycline analogs, olvanil and olvanil analogs, retro-olvanil and retro-olvanil analogs, olvanil carbamate, NSAID-ache, budesonide and budesonide analogs, methylprenisolone and methylprenisolone analogs and dexamethasone and dexamethasone analogs. Anticancer drugs such as camptothecin, carboplatin, doxorubicin, paclitaxel; HIV Protease Inhibitors including: saquinavir mesylate, amprenavir, ritonavir, indinavir, nelfinavir mesylate, tipranavir, darunavir and atazanavir sulfate; monoclonal antibodies; imaging agents including: coloring dyes like FD and C dyes, or visible/near infrared fluorescence dyes like fluorescein, methylene blue, rhodamine, dansyl, Alexa, cyanine dyes, Hilyte, indocyanine green and the like. In certain embodiments, the agent is doxorubicin. In certain embodiments, the agent is coupled to the PEG by a linking group selected from the group consisting of peptide linkers, self-immolative linkers, acid sensitive linkers, bifunctional organic linking agents, bifunctional inorganic crosslinking agents, Leu-Gly, Glu(Leu-Gly)2, Arg-Gly-Asp-Cys, Gly-Arg-Gly-Asp-Ser, Gly-Arg-Gly-Asp-Ser-Pro, cyclic Arg-Gly-Asp-Tyr-Lys, or any peptide with Arg-Gly-Asp. In certain embodiments, the doxorubicin is coupled to the PEG by a linker selected from the group consisting of Leu-Gly, Glu(Leu-Gly)2, Arg-Gly-Asp-Cys, Gly-Arg-Gly-Asp-Ser, Gly-Arg-Gly-Asp-Ser-Pro, cyclic Arg-Gly-Asp-Tyr-Lys, or any peptide with Arg-Gly-Asp.

In accordance with any of the above embodiments, the invention further comprises a targeting moiety. In certain other embodiments, the targeting moiety is a peptide. In certain other embodiments, the peptide is an RGD peptide.

In accordance with any of the above embodiments, the invention further comprises a surface modification. In certain embodiments, the surface modification alters a property selected from the group consisting of surface charge, surface charge density, surface hydrophobicity, and surface charge and hydrophobicity combined. In certain embodiments, surface modifications will affect body, tissue, organ and cell interactions, as well as distribution and persistence of nanogel particles and aggregated nanogel particles.

The invention is also directed to aggregated nanogel particles, comprising multi-arm polyalkylene oxide crosslinked via disulfide and/or thioether bonds, wherein the nanogel particles are aggregated via hydrophobic interactions, and wherein the aggregated nanogel particles have a particle size of about 10 nm to about 1 mm. In certain other embodiments, the particles have a particle size of about 20 to about 30 nm. In certain other embodiments, the particle size ranges from about 20 to about 200 nm for targeting tumor micro vasculature and lymph nodes. In certain other embodiments, the particle size ranges from about 100 to about 1000 microns for targeting micro metastasis. In certain other embodiments, the particle size ranges from about 1 to about 5 microns for targeting spleen. In certain other embodiments, the particle size ranges from about 2 to about 10 microns for liver. In certain other embodiments, the particle size ranges from about 5 to about 100 microns for targeting pulmonary vasculature. In certain other embodiments, the particle size ranges from about 5 to about 1000 microns for achieving intraductal breast retention.

In accordance with any of the above embodiments, the invention further comprises surface modification. In certain embodiments, the surface modification alters a property selected from the group consisting of surface charge, surface charge density, surface hydrophobicity, surface charge and hydrophobicity combined, surface adhesion, body/tissue distribution or intracellular trafficking of aggregated nanogel particles.

In accordance with any of the above embodiments, the multi-arm polyalkylene oxide is PEG. In certain other embodiments, the PEG is a multi-arm PEG with molecular weight range 1000-100,000 Da. In certain other embodiments, the PEG is functionalized with terminal active ester (N-hydroxy succinimidy ester, for example), amine, thiol, activated thiol (thiopyridine activated for example), maleimide, vinyl sulfone, aldehyde, aminooxy, hydrazine, tosyl, idoacetamide, and p-nitrophenyl group.

In accordance with any of the above embodiments, the invention further comprises an agent. In certain embodiments, the agent is selected from the group consisting of indomethacin, sancycline, a sancycline analog, olvanil, an olvanil analog, retro-olvanil, a retro-olvanil analog, olvanil carbamate, budesonide, a budesonide analog, methylprednisolone, a methylprenisolone analog, dexamethasone, a dexamethasone analog, camptothecin, carboplatin, doxorubicin, paclitaxel, saquinavir mesylate amprenavir ritonavir, indinavir, nelfinavir, mesylate, tipranavir, darunavir, atazanavir sulfate, a coloring dye, an FD and C dye, a visible/near infrared fluorescence dye, fluorescein, methylene blue, rhodamine, dansyl, Alexa, a cyanine dye, Hilyte, indocyanine green, and combinations thereof. In certain other embodiments, the agent is doxorubicin.

In accordance with any of the above embodiments, the agent is coupled to the PEG by a linking group selected from the group consisting of peptide linkers, self-immolative linkers, acid sensitive linkers, multifunctional organic linking agents, multifunctional inorganic crosslinking agents, Leu-Gly, Glu(Leu-Gly)2, Arg-Gly-Asp-Cys, Gly-Arg-Gly-Asp-Ser, Gly-Arg-Gly-Asp-Ser-Pro, cyclic Arg-Gly-Asp-Tyr-Lys, or any peptide with Arg-Gly-Asp. In certain embodiments, the doxorubicin is coupled to the PEG by a linker selected from the group consisting of Leu-Gly, Glu(Leu-Gly)2, Arg-Gly-Asp-Cys, Gly-Arg-Gly-Asp-Ser, Gly-Arg-Gly-Asp-Ser-Pro, cyclic Arg-Gly-Asp-Tyr-Lys, or any peptide with Arg-Gly-Asp.

In accordance with any of the above embodiments, the invention further comprises a targeting moiety. In certain other embodiments, the targeting moiety is a peptide. In certain other embodiments, the peptide is an RGD peptide.

The invention is also directed to a colloidal dispersion, comprising: nanogel particles comprising multi-arm polyalkylene oxide crosslinked via disulfide and/or thioether bonds and having a mean particle size of greater than about 1 nm; and aggregated nanogel particles, wherein the nanogel particles are aggregated via hydrophobic interactions and wherein the aggregated nanogel particles have a particle size of about 10 nm to about 9000 nm. In certain embodiments, the nanogel particles further comprise a surface modification. In certain embodiments, the surface modification alters a property selected from the group consisting of surface charge, surface charge density, surface hydrophobicity, surface charge and hydrophobicity combined, surface dehension, body/tissue distribution or intracellular trafficking of NPs and ANPs. In certain embodiments, the nanogel particles further comprise an agent. In certain embodiments, the agent is selected from the group consisting of indomethacin, sancycline, a sancycline analog, olvanil, an olvanil analog, retro-olvanil, a retro-olvanil analog, olvanil carbamate, budesonide, a budesonide analog, methylprednisolone, a methylprenisolone analog, dexamethasone, a dexamethasone analog, camptothecin, carboplatin, doxorubicin, paclitaxel, saquinavir mesylate, amprenavir, ritonavir, indinavir, nelfinavir mesylate, tipranavir, darunavir, atazanavir sulfate, a coloring dye, an FD and C dye, a visible/near infrared fluorescence dye, fluorescein, methylene blue, rhodamine, dansyl, Alexa, a cyanine dye, Hilyte, indocyanine green, and combinations thereof. In certain embodiments, the agent is doxorubicin. In certain embodiments, the agent is coupled to the PEG by a linking group selected from the group consisting of Leu-Gly, Glu(Leu-Gly)2, Arg-Gly-Asp-Cys, Gly-Arg-Gly-Asp-Ser, Gly-Arg-Gly-Asp-Ser-Pro, cyclic Arg-Gly-Asp-Tyr-Lys, or any peptide with Arg-Gly-Asp.

In accordance with any of the above embodiments, the nanogel particles further comprise a targeting moiety. In certain embodiments, the targeting moiety is a peptide. In certain embodiments, the peptide is an RGD peptide.

The invention is also directed to a method of making the nanocarrier in accordance with any of the above embodiments comprising linking irreversibly or reversibly an agent to multi-arm functionalized polyalkylene oxide polymer with a molecular weight ranging from 1,000 to 100,000 Da either directly or through a linking group selected from the group consisting of peptide linkers, enzyme self-immolative linkers, acid and base sensitive linkers, multifunctional organic linking agents, multifunctional inorganic crosslinking agents and/or peptidic backbones represented as: $CH_3CO-(X-Z-Z)_x-(Y-Z-Z)_y-CONH_2$, where X=Lys, Glu, Asp or diaminobutyric acid; Y=Cys, homocysteine or 1-amino-2-methyl-2-propanethiol; Z=β-Ala, Gly, Ala, or GABA (gamma-amino butyric acid); x and y are interchangeable; x is between 1 to 4; y is between 1 to 4; minimum no. of Z-spacer on the peptide backbone=2; maximum no. of Z-spacer on the peptide backbone=4 in an aqueous or organic solvent with pH ranging from 6 to 12 using any coupling reagents, wherein the reaction mixture is stirred from 30 mins to 24 hours at a temperature greater than about 4° C. to less than about 40° C., followed by purification and lyophilization. In certain embodiments, the nanocarriers has a molar ratio of agent to multi-arm polyalkylene oxide greater than about 1:1 and an aqueous solubility of at least about 0.1 mg/ml.

The invention is also directed to a process of making the nanogel particles in accordance with any of the above embodiments comprising reversibly or irreversibly crosslinking a multi-arm functionalized polyakylene oxide polymer with a molecular weight ranging from 1,000 to 100,000 Da using a multi-arm crosslinker containing mutually reactive functional groups in an aqueous solvent with pH ranging from about 6 to about 12, containing a surfactant in a concentration of about 0.01%-1.0%, wherein the reaction mixture is initially dispersed up to about 60 minutes, and then is stirred for up to 24 hours at a temperature range from greater than about 4 to less than about 40° C.

The invention is also directed to a method of treating and/or preventing a disease or condition, comprising administering to an animal or human in need thereof a composition comprising the nanocarrier in accordance with any of the above embodiments, wherein the nanocarrier comprises an amount of the agent sufficient to treat and/or prevent the disease.

The invention is also directed to a method of treating and/or preventing a disease or condition, comprising administering to an animal or human in need thereof a composition comprising the nanogel particles in accordance with any of the above embodiments, wherein the nanogel particles comprise an amount of the agent sufficient to treat and/or prevent the disease.

The invention is also directed to a method of treating and/or preventing a disease or condition, comprising administering to an animal or human in need thereof a composition comprising the aggregated nanogel particles in accordance with any of the above embodiments, wherein the aggregated nanogel particles comprise an amount of the agent sufficient to treat and/or prevent the disease.

The invention is also directed to a method of treating and/or preventing a disease or condition, comprising administering to an animal or human in need thereof a composition comprising the colloidal or coarse dispersion in accordance with any of the above embodiments, wherein the colloidal or coarse dispersion comprises an amount of the agent sufficient to treat and/or prevent the disease.

A nanocarrier is disclosed in accordance with an embodiment of the invention. The nanocarrier comprises an agent coupled to a multi-arm polyalkylene oxide, wherein the molar ratio of agent to multi-arm polyalkylene oxide is greater than about 1:1 and the nanocarrier exhibits an aqueous solubility of at least about 0.1 mg/ml. In variations to the nanocarrier, the molar ratio of agent to multi-arm polyalkylene oxide is greater than about 1.2:1, greater than about 1.5:1, greater than about 1.8:1, or greater than about 2:1. The aqueous solubility of the nanocarrier may be at least about 10 mg/ml, at least about 33 mg/ml, at least about 100 mg/ml, or at least about 1000 mg/ml.

In preferred embodiments of the nanocarrier, the multi-arm polyalkylene oxide is PEG. In some embodiments, the PEG is a 4- or 8-arm PEG. The PEG may be functionalized with terminal SH groups.

The nanocarrier preferably comprises an agent selected from the group consisting of anti-inflammatory drugs, NSAID analogs, NSAID-ache (NSAID-acetylcholinesterase complexes, steroidal anti-inflammatory drugs, anticancer drugs, HIV Protease Inhibitors, Monoclonal antibodies, imaging agents, and combinations thereof. In certain other embodiments, the agent is selected from the group consisting of one or more of the following: indomethacin, sancycline, a sancycline analog, olvanil, an olvanil analog, retro-olvanil, a retro-olvanil analog, olvanil carbamate, budesonide, a budesonide analog, methylprednisolone, a methylprenisolone analog, dexamethasone, a dexamethasone analog, camptothecin, carboplatin, doxorubicin, paclitaxel, saquinavir mesylate, amprenavir, ritonavir, indinavir, nelfinavir mesylate, tipranavir, darunavir, atazanavir sulfate, a coloring dye, an FD and C dye, a visible/near infrared fluorescence dye, fluorescein, methylene blue, rhodamine, dansyl, Alexa, a cyanine dye, Hilyte, indocyanine green, and combinations thereof. More preferably, the agent is doxorubicin.

The agent may be coupled to the PEG by a linking group selected from the group consisting of peptide linkers, enzyme self-immolative linkers, acid and base sensitive linkers, multifunctional organic linking agents, multifunctional inorganic crosslinking agents and/or peptidic backbones represented as: $CH_3CO—(X—Z—Z)_x—(Y—Z—Z)_y—CONH_2$, where X=Lys, Glu, Asp or diaminobutyric acid; Y=Cys, homocysteine or 1-amino-2-methyl-2-propanethiol; Z=β-Ala, Gly, Ala, or GABA (gamma-amino butyric acid); x and y are interchangeable; x is between 1 to 4; y is between 1 to 4; minimum no. of Z-spacer on the peptide backbone=2; maximum no. of Z-spacer on the peptide backbone=4.

In variations, the nanocarrier may further comprise a targeting moiety. The targeting moiety may be a peptide, and preferably such a peptide is an RGD peptide. In certain other embodiments, the targeting moiety is selected from the group consisting of an RGD peptide, a DV3 (LGASWHRPDKC) peptide, a LYP peptide (CGNKRTRGC), a membrane binding domain of IGFBP3 (QCRPSKGRKRGFCW), fMLF, mannose, transferrin ligand, and a monoclonal antibody.

A nanogel particle is disclosed in accordance with an embodiment of the invention, comprising multi-arm polyalkylene oxide crosslinked via disulfide and/or thioether bonds, wherein the nanogel particle has a mean particle size of greater than about 1 nm to about 250 nm. In certain embodiments, the nanogel particles size ranges from about 20 to about 200 nm targeting tumors and lymph nodes. In certain embodiments, the nanogel particle size is greater that about 5 nm to about 250 nm. In certain embodiments, the nanogel particle size ranges from about 20 to about 200 nm targeting tumors and lymph nodes. In certain embodiments, the mean particle size is greater that about 10 nm to about 250 nm. In certain embodiments, the mean particle size is from about 20 nm to about 30 nm.

In accordance with any of the above embodiments, the multi-arm polyalkylene oxide is PEG. In certain embodiments, the PEG is a 4- or 8-arm PEG. In certain embodiments, the PEG is functionalized with terminal SH groups.

In accordance with any of the above embodiments, nanogel particle further comprises an agent. In certain embodiments, the agent is selected from the group consisting of indomethacin, sancycline, a sancycline analog, olvanil, an olvanil analog, retro-olvanil, a retro-olvanil analog, olvanil carbamate, budesonide, a budesonide analog, methylprednisolone, a methylprenisolone analog, dexamethasone, a dexamethasone analog, camptothecin, carboplatin, doxorubicin, paclitaxel, saquinavir mesylate, amprenavir, ritonavir, indinavir, nelfinavir mesylate, tipranavir, darunavir, atazanavir sulfate, a coloring dye, an FD and C dye, a visible/near infrared fluorescence dye, fluorescein, methylene blue, rhodamine, dansyl, Alexa, a cyanine dye, Hilyte, indocyanine green, and combinations thereof. In certain embodiments, the agent is doxorubicin.

In certain other embodiments, the agent is coupled to the PEG by a linking group selected from the group consisting of peptide linkers, enzyme self-immolative linkers, acid and base sensitive linkers, multifunctional organic linking agents, multifunctional inorganic crosslinking agents and/or peptidic backbones represented as: $CH_3CO—(X—Z—Z)_x—(Y—Z—Z)_y—CONH_2$, where X=Lys, Glu, Asp or diaminobutyric acid; Y=Cys, homocysteine or 1-amino-2-methyl-2-propanethiol; Z=β-Ala, Gly, Ala, or GABA (gamma-amino butyric acid); x and y are interchangeable; x is between 1 to 4; y is between 1 to 4; minimum no. of Z-spacer on the peptide backbone=2; maximum no. of Z-spacer on the peptide backbone=4. In certain other embodiments, the doxorubicin is coupled to the PEG by a linker selected from the group consisting of Leu-Gly, Glu(Leu-Gly)2, Arg-Gly-Asp-Cys, Gly-Arg-Gly-Asp-Ser, Gly-Arg-Gly-Asp-Ser-Pro, cyclic Arg-Gly-Asp-Tyr-Lys, or any peptide with Arg-Gly-Asp.

In certain other embodiments, the nanogel particle further comprises a targeting moiety. In certain other embodiments, the targeting moiety is a peptide. In certain other embodiments, the targeting moiety is selected from the group consisting of an RGD peptide, a DV3 (LGASWHRPDKC) peptide, a LYP peptide (CGNKRTRGC), a membrane binding domain of IGFBP3 (QCRPSKGRKRGFCW), fMLF, mannose, transferrin ligand, and a monoclonal antibody.

In accordance with any of the above embodiments, the nanogel particle further comprises a surface modification. In certain embodiments, the surface modification the surface modification alters a property selected from the group consisting of surface charge, surface charge density, surface hydrophobicity, and surface charge and hydrophobicity combined.

The invention is also directed to aggregated nanogel particles, comprising multi-arm polyalkylene oxide which are crosslinked, wherein the nanogel particles are aggregated, and wherein the aggregated nanogel particles have a particle size of from about 100 nm to about 1 mm. In certain embodiments, the aggregated nanogel particles, comprise multi-arm polyalkylene oxide crosslinked via disulfide and/or thioether bonds, wherein the nanogel particles are aggregated via hydrophobic interactions, and wherein the aggregated nanogel particles have a particle size of from about 100 nm to about 1 mm. In certain embodiments, the aggregated nanogel particle size ranges from about 100 to about 200 nm targeting tumors and lymph nodes. In certain embodiments, the aggregated nanogel particle size ranges from about 1 to about 5 microns for targeting retention in the spleen. In certain embodiments, the aggregated nanogel particle size ranges from about 2 to about 10 microns for targeting retention in the liver. In certain embodiments, the aggregated nanogel particle size ranges from about 5 to about 100 microns for targeting retention in lung. In certain embodiments, the aggregated nanogel particle size ranges from about 5 to about 1000 microns for targeting retention in the breast duct and breast tissue.

In accordance with any of the above objects, the aggregated nanogel particles further comprising a surface modification. In certain embodiments, the surface modification alters a property selected from the group consisting of surface charge, surface charge density, surface hydrophobicity, and surface charge and hydrophobicity combined.

In certain embodiments, multi-arm polyalkylene oxide is PEG. In certain other embodiments, the PEG is a 4- or 8-arm PEG. In still other embodiments, the PEG is functionalized with terminal SH groups. In certain other embodiments, the aggregated nanogel further comprise an agent. In certain embodiments, the agent is selected from the group consisting of indomethacin, sancycline, a sancycline analog, olvanil, an olvanil analog, retro-olvanil, a retro-olvanil analog, olvanil carbamate, budesonide, a budesonide analog, methylprednisolone, a methylprenisolone analog, dexamethasone, a dexamethasone analog, camptothecin, carboplatin, doxorubicin, paclitaxel, saquinavir mesylate, amprenavir, ritonavir, indinavir, nelfinavir mesylate, tipranavir, darunavir, atazanavir sulfate, a coloring dye, an FD and C dye, a visible/near infrared fluorescence dye, fluorescein, methylene blue, rhodamine, dansyl, Alexa, a cyanine dye, Hilyte, indocyanine green, and combinations thereof. In certain embodiments, the agent is doxorubicin.

In certain embodiments, the agent is coupled to the PEG by a linking group selected from the group consisting of peptide linkers, enzyme self-immolative linkers, acid and base sensitive linkers, multifunctional organic linking agents, multifunctional inorganic crosslinking agents and/or peptidic backbones represented as: $CH_3CO—(X—Z—Z)_x—(Y—Z—Z)_y—CONH_2$, where X=Lys, Glu, Asp or diaminobutyric acid; Y=Cys, homocysteine or 1-amino-2-methyl-2-propanethiol; Z=β-Ala, Gly, Ala, or GABA (gamma-amino butyric acid); x and y are interchangeable; x is between 1 to 4; y is between 1 to 4; minimum no. of Z-spacer on the peptide backbone=2; maximum no. of Z-spacer on the peptide backbone=4.

In certain embodiments, doxorubicin is coupled to the PEG by a linker selected from the group consisting of Leu-Gly, Glu(Leu-Gly)2, Arg-Gly-Asp-Cys, Gly-Arg-Gly-Asp-Ser, Gly-Arg-Gly-Asp-Ser-Pro, cyclic Arg-Gly-Asp-Tyr-Lys, or any peptide with Arg-Gly-Asp.

In accordance with any of the above embodiments, the aggregated nanogel particles, further comprise a targeting moiety. In certain embodiments, the targeting moiety is a peptide.

In certain embodiments, the targeting moiety is selected from the group consisting of an RGD peptide, a DV3 (LGASWHRPDKC) peptide, a LYP peptide (CGNKRTRGC), a membrane binding domain of IGFBP3 (QCRPSKGRKRGFCW), fMLF, mannose, transferrin ligand, and a monoclonal antibody.

The invention is also directed to a colloidal or coarse dispersion, comprising: nanogel particles comprising multi-arm polyalkylene oxide which are crosslinked, wherein the nanogel particles are aggregated, and wherein the nanogel particles have a mean particle size of greater than about 1 nm to about 250 nm; and aggregated nanogel particles, wherein the nanogel particles are aggregated and wherein the aggregated nanogel particles have a particle size of about 100 nm to about 1 mm.

The invention is also directed to a colloidal or coarse dispersion, comprising nanogel particles comprising multi-arm polyalkylene oxide crosslinked via disulfide and/or thioether bonds and having a mean particle size of greater than about 1 nm to about 250 nm; and aggregated nanogel particles, wherein the nanogel particles are aggregated via hydrophobic interactions and wherein the aggregated nanogel particles have a particle size of about 100 nm to about 1 mm.

In certain embodiments in accordance with any of the above, the dispersion further comprises a surface modification. In certain embodiments, the surface modification alters a property selected from the group consisting of surface charge, surface charge density, surface hydrophobicity, and surface charge and hydrophobicity combined.

In certain embodiments, the dispersion further comprise an agent.

In certain embodiments, the agent is selected from the group consisting of indomethacin, sancycline, a sancycline analog, olvanil, an olvanil analog, retro-olvanil, a retro-olvanil analog, olvanil carbamate, budesonide, a budesonide analog, methylprednisolone, a methylprenisolone analog, dexamethasone, a dexamethasone analog, camptothecin, carboplatin, doxorubicin, paclitaxel, saquinavir mesylate, amprenavir, ritonavir, indinavir, nelfinavir mesylate, tipranavir, darunavir, atazanavir sulfate, a coloring dye, an FD and C dye, a visible/near infrared fluorescence dye, fluorescein, methylene blue, rhodamine, dansyl, Alexa, a cyanine dye, Hilyte, indocyanine green, and combinations thereof.

In certain embodiments, the agent the agent is doxorubicin.

In certain embodiments, the agent the agent is coupled to the PEG by a linking group selected from the group consisting of peptide linkers, enzyme self-immolative linkers, acid and base sensitive linkers, multifunctional organic linking agents, multifunctional inorganic crosslinking agents and/or peptidic backbones represented as: $CH_3CO—(X—Z—Z)_x—(Y—Z—Z)_y—CONH_2$, where X=Lys, Glu, Asp or diaminobutyric acid; Y=Cys, homocysteine or 1-amino-2-methyl-2-propanethiol; Z=β-Ala, Gly, Ala, or GABA (gamma-amino butyric acid); x and y are interchangeable; x is between 1 to 4; y is between 1 to 4; minimum no. of Z-spacer on the peptide backbone=2; maximum no. of Z-spacer on the peptide backbone=4.

In certain embodiments, the doxorubicin is coupled to the PEG by a linker selected from the group consisting of Leu-Gly, Glu(Leu-Gly)2, Arg-Gly-Asp-Cys, Gly-Arg-Gly-Asp-Ser, Gly-Arg-Gly-Asp-Ser-Pro, cyclic Arg-Gly-Asp-Tyr-Lys, or any peptide with Arg-Gly-Asp.

In certain embodiments, the agent the nanogel particles further comprise a targeting moiety.

In certain embodiments, the targeting moiety is a peptide.

In certain embodiments, the targeting moiety is selected from the group consisting of an RGD peptide, a DV3 (LGASWHRPDKC) peptide, a LYP peptide (CGNKRTRGC), a membrane binding domain of IGFBP3 (QCRPSKGRKRGFCW), fMLF, mannose, transferrin ligand, and a monoclonal antibody.

In accordance with any of the above embodiments, the invention is also directed to a method of making the nanocarrier comprising: (i) directly linking an agent to multi-arm functionalized polyalkylene oxide polymer with a molecular weight ranging from 1,000 to 100,000 Da, in an aqueous or organic solvent with pH ranging from 6 to 12 using a coupling reagent, (ii) stirring the reaction mixture for a time period from 30 mins to 24 hours at a temperature greater than about 4° C. to less than about 40° C., and (iii) purification and lyophilization to obtain the nanocarrier.

In accordance with any of the above embodiments, the invention is also directed to a method of making the nanocarrier comprising, comprising: (i) linking an agent to multi-arm functionalized polyalkylene oxide polymer with a molecular weight ranging from 1,000 to 100,000 Da through a linking group selected from the group consisting of peptide linkers, enzyme self-immolative linkers, acid and base sensitive linkers, multifunctional organic linking agents, multifunctional inorganic crosslinking agents and/or peptidic backbones represented as: $CH_3CO-(X-Z-Z)_x-(Y-Z-Z)_y-CONH_2$, where X=Lys, Glu, Asp or diaminobutyric acid; Y=Cys, homocysteine or 1-amino-2-methyl-2-propanethiol; Z=β-Ala, Gly, Ala, or GABA (gamma-amino butyric acid); x and y are interchangeable; x is between 1 to 4; y is between 1 to 4; minimum no. of Z-spacer on the peptide backbone=2; maximum no. of Z-spacer on the peptide backbone=4, in an aqueous or organic solvent with pH ranging from 6 to 12 using a coupling reagent, (ii) stirring the reaction mixture for a time period from 30 mins to 24 hours at a temperature greater than about 4° C. to less than about 40° C., and (iii) purification and lyophilization to obtain the nanocarrier. The bond between the agent and the multi-arm functionalized polyalkylene oxide polymer is reversible or irreversible. In certain embodiments, at least one of the bonds in the nanocarrier is reversible.

In accordance with any of the above embodiments, the invention is also directed to a method of making a nanogel particle, comprising: (i) cross-linking a multi-arm functionalized polyakylene oxide polymer with a molecular weight ranging from 1,000 to 100,000 Da using a multi-arm crosslinker containing mutually reactive functional groups in an aqueous solvent with pH ranging from 6 to 12 containing a surfactant 0.01%-1.0%, (ii) dispersing the reaction mixture for up to 60 minutes, (iii) stirring the reaction mixture for up to 24 hours at >4 but less than 40° C. and (iv) collecting the nanogel particles. In certain embodiments, the crosslinking is reversible or irreversible.

In certain embodiments, the method comprises the steps of (i) cross-linking a multi-arm functionalized polyakylene oxide polymer with a molecular weight ranging from 1,000 to 100,000 Da using a multi-arm crosslinker containing mutually reactive functional groups in an aqueous solvent with pH ranging from 6 to 12 containing a surfactant 0.01%-1.0%, (ii) stirring the reaction mixture for more then about 1 day to about 30 days at >4 but less than 40° C. until the ANP (aggregated nanoparticle) reaches the target size (iii) crosslinking the reactive group of the ANP with a cap comprising a polyalkylene oxide (e.g., PEG) containing a complimentary reactive group to the reactive group on the ANP without a further reactive group, effectively stabilizing the ANP and ceasing further growth of the ANP and (iv) collecting the aggregated nanogel particles. In certain embodiments, the crosslinking in step (i) is reversible or irreversible.

In certain embodiments, the method comprises the steps of: (i) cross-linking a multi-arm functionalized polyakylene oxide polymer with a molecular weight ranging from 1,000 to 100,000 Da using a multi-arm crosslinker containing mutually reactive functional groups in an aqueous solvent with pH ranging from 6 to 12 containing a surfactant 0.01%-1.0%, (ii) stirring the reaction mixture for more then about 1 day to about 30 days at >4 but less than 40° C. until the ANP (aggregated nanoparticle) reaches a size that is larger than the target size (iii) crosslinking the reactive group of the ANP with a cap comprising a polyalkylene oxide (e.g., PEG) containing a complimentary reactive group to the reactive group on the ANP without a further reactive group, effectively stabilizing the ANP and ceasing further growth of the ANP (iv) reducing the size of the ANP to a target size and (v) collecting the aggregated nanogel particles.

In certain embodiments, the method comprises the crosslinking in step (i) is reversible or irreversible.

In certain embodiments, the method comprises step (v) is achieved by sonication.

In certain embodiments, the method comprises step (iii) is repeated after step (iv).

A method of modifying the surface of aggregated nanogel particles, comprising: bonding the mutually reactive groups of the polyalkylene oxide (e.g., PEG) with the complimentary reactive group on a molecular group which imparts a property selected from the group consisting of: charge, charge density, hydrophobicity, hydrophilicity or a combination thereof, to the ANP.

In certain embodiments, the method comprises the molecular group is an amino acid selected from the group consisting of hydrophilic and hydrophobic amino acids.

In accordance with any of the above embodiments, the invention is also directed to a method of treating and/or preventing a disease or condition, comprising administering to an animal or human in need thereof a composition comprising the nanocarrier, wherein the nanocarrier comprises an amount of the agent sufficient to treat and/or prevent the disease.

In accordance with any of the above embodiments, the invention is also directed to a method of treating and/or preventing a disease or condition, comprising administering to an animal or human in need thereof a composition comprising the nanogel particles, wherein the nanogel particles comprise an amount of the agent sufficient to treat and/or prevent the disease.

In accordance with any of the above embodiments, the invention is also directed to a method of treating and/or preventing a disease or condition, comprising administering to an animal or human in need thereof a composition comprising the aggregated nanogel particles wherein the aggregated nanogel particles comprise an amount of the agent sufficient to treat and/or prevent the disease.

In accordance with any of the above embodiments, the invention is also directed to a method of treating and/or preventing a disease or condition, comprising administering to an animal or human in need thereof a composition comprising the colloidal or coarse dispersion of wherein the dispersion comprises an amount of the agent sufficient to treat and/or prevent the disease.

In certain embodiments, the invention is directed to a composition comprising a nanocarrier comprising an agent coupled to a multi-arm polyalkylene oxide, wherein the molar ratio of agent to multi-arm polyalkylene oxide is greater than about 1:1 and the nanocarrier exhibits an aqueous solubility of at least about 0.1 mg/ml. In certain other embodiments, the molar ratio is greater than about 1.2:1. In certain other embodiments, the molar ratio is greater than about 2:1. In certain other embodiments, the aqueous solubility is at least about 10 mg/ml. In certain other embodiments, the molar ratio is greater than about 2:1. In certain other embodiments, the aqueous solubility is at least about 1000 mg/ml.

In accordance with the above embodiments, the composition comprises multiple nanocarriers, wherein the multi-arm polyalkylene oxide of the nanocarriers is crosslinked via bond such as a disulfide and/or thioether bond such that the composition is comprised of nanogel particles having a mean particle size of greater than about 1 nm to about 250 nm. In certain other embodiments, the nanogel particles are aggregated, (e.g., via hydrophobic interactions), and the aggregated nanogel particles have a particle size of about 100 nm to about 1 mm.

In certain other embodiments, the multi-arm polyalkylene oxide is PEG. In still other embodiments, the multi-arm polyalkylene oxide is a 4-arm or 8-arm PEG. In certain preferred embodiments, the 8-arm PEG is functionalized with terminal SH groups.

In accordance with any of the above embodiments, the agent is selected from the group consisting of: anti-inflammatory drugs, NSAID analogs, NSAID-ache (NSAID-acetylcholinesterase inhibitor complexes, steroidal anti-inflammatory drugs, anticancer drugs, HIV Protease Inhibitors, Monoclonal antibodies, imaging agents, and combinations thereof. In certain other embodiments, the agent is any agent that is stabile or can be made stable within the nanocarrier, nanogel particle, aggregated nanogel particle, or colloidal or coarse dispersion system of the present invention. In certain other embodiments, the agent is selected from the group consisting of one or more of the following: indomethacin, sancycline, a sancycline analog, olvanil, an olvanil analog, retro-olvanil, a retro-olvanil analog, olvanil carbamate, budesonide, a budesonide analog, methylprednisolone, a methylprenisolone analog, dexamethasone, a dexamethasone analog, camptothecin, carboplatin, doxorubicin, paclitaxel, saquinavir mesylate, amprenavir, ritonavir, indinavir, nelfinavir mesylate, tipranavir, darunavir, atazanavir sulfate, a coloring dye, an FD and C dye, a visible/near infrared fluorescence dye, fluorescein, methylene blue, rhodamine, dansyl, Alexa, a cyanine dye, Hilyte, indocyanine green, and combinations thereof.

In accordance with any of the above objects, the invention is also directed to a composition comprising nanogel particles, comprising multi-arm polyalkylene oxide crosslinked via disulfide and/or thioether bonds, wherein the nanogel particles have a mean particle size from about greater than 1 nm to about 100 nm.

In accordance with any of the above objects, the invention is also directed to a composition comprising agglomerated nanogel particles comprising multi-arm polyalkylene oxide crosslinked via disulfide and/or thioether bonds, wherein the agglomerated nanogel particles have a mean particle size from about 100 nm to about 1 mm.

BRIEF DESCRIPTION OF THE DRAWINGS

FIG. 1. Is a schematic of the preparation of PEGylated Dox nanocarrier {PEG$_{20kDa}$[Glu(Leu-Gly-Dox)$_2$]$_2$ (4 copy Dox)}.

FIG. 2. Is a schematic of the preparation of PEGylated Dox nanocarrier {PEG$_{20kDa}$(RGDC-Dox)$_4$ (4 copy Dox)}.

FIG. 3. Is a schematic of the synthesis of stabilized aggregated nano particles (ANPs).

FIG. 4. NPs size determination using Dynamic Light Scattering (DLS).

FIG. 5. Morphology and size of NPs using Transmission Electron Microscope (TEM), Particle size: 20-100 nm.

FIG. 6. NPs size determination using Dynamic Light Scattering (DLS) spectrophotometer.

FIG. 7. Morphology and size of NPs using Transmission Electron Microscopy (TEM), particle size: 20-40 nm.

FIG. 8. Morphology and size of NPs using Transmission Electron Microscopy (TEM), particle size: 20-300 nm.

FIG. 9. NPs size determination using Dyanamic Light Scattering (DLS) spectrophotometer. NPs preparation using surfactant and stirring time of 1 day, 2 days, and 3 days.

FIG. 10. NPs size determination using Dyanamic Light Scattering (DLS) spectrophotometer. NPs were prepared using surfactant, sonication and stirring time of 1 day, 2 days, and 3 days.

FIG. 11. NPs size determination using Dynamic Light Scattering (DLS) spectrophotometer. Effects of surfactant, sonication and stirring time on ANPs size is shown.

FIG. 12. Morphology and size of ANPs (~10 micron) using Transmission Electron Microscopy (TEM).

FIG. 13. Morphology and size of ANPs (~18 micron) using Transmission Electron Microscopy (TEM).

FIG. 14. Morphology and size of ANPs (~24 micron) using Transmission Electron Microscopy (TEM).

FIG. 15. Morphology and size of ANPs (~24 micron) using Transmission Electron Microscopy (TEM).

FIG. 16. Size determination of sonicated ANPs using coulter counter.

FIG. 17. Size determination of sonicated ANPs using coulter counter.

FIG. 18. Size determination of sonicated ANPs using coulter counter.

FIG. 19. Size determination of sonicated ANPs using coulter counter.

FIG. 20. Biodistribution studies of DYE-ANPs (particle size: 50-60 μm) in rats using IVIS 100 optical imager.

FIG. 21. Biodistribution studies of DYE-ANPs (particle size: 30-50 μm) in rats using IVIS 100 optical imager.

FIG. 22. Biodistribution studies of DYE-ANPs (particle size: 10-20 μm) in rats using IVIS 100 optical imager.

FIG. 23. Biodistribution studies of DYE-ANPs (particle size: 10-20 μm) in mice using IVIS 100 optical imager.

FIG. 24. Lung histology following ANP injection (20 μm). Magnification 100×.

DEFINITIONS

Unless characterized otherwise, technical and scientific terms used herein have the same meaning as commonly understood by one of ordinary skill in the art to which this invention belongs. For purposes of the present invention, the following terms are described below.

"PEG" is used herein as an abbreviation for polyethylene glycol. PEGs are included within the broader class of polyalkylene oxides, which include PEG as well as polypropylene glycols, and polyglycol copolymers. PEG can have a range of molecular weights. The PEG molecular weight range contemplated for use in the present invention is from about 1000 to about 100,000 Da. PEG can be linear, branched, multi-arm, or a combination of branched and multi-arm. Various PEGs can be derivatized with various groups, such as activated ester (N-hydroxy succinimidy ester, for example), p-nitrophenyl, aldehyde, amine, thiol, activated thiol (thiopyridine activated thiol, for example), vinyl sulfone, maleimide, aminooxy, hydrazine, tosyl, and idoacetamide.

"Scaffolds" include substituted polyalkylene oxides, preferably PEGs, such as those having thiol or other functional groups suitable for attachment of an agent and/or for cross-linking.

"Nanocarrier" includes scaffolds having an agent attached.

"Nanogel particles" include micron and submicron-sized PEG particles. These particles can be generated by cross-linking scaffolds or nanocarriers under suitable conditions. Nanogel particles can have agents associated with them.

"Aggregated nanogel particles" also referred to as "ANPs" includes nanogel particles that have associated together, in some cases upon input of mechanical energy (e.g., stirring), such as by hydrophobic interaction or other noncovalent interaction.

"Surface modification" includes chemical treatment of nanogel particles or aggregated nanogel particles to modify, for example, the surface charge/charge density, hydrophobicity/hydrophilicity, or both. The actual chemical treatment can be performed on the final material, such as the nanogel particle, or ANP, or it be performed on a precursor material, such as the scaffold or nanocarrier.

"Agent" includes without limitation any therapeutic, palliative, cosmetic and/or prophylactic compositions, including without limitation small molecules, drugs, biologicals, recombinant peptides, proteins and nucleic acids and immunochemicals, as well as diagnostic and imaging compositions, as may be further indicated by the context. In some uses, the term can relate to other types of compositions, as indicated by the context.

Solubility Terms

Unless indicated otherwise, either expressly or by implication, the following solubility terms are used as described in Table 1 below (Reproduced from Stegemann, et al., "When Poor Solubility Becomes an Issue: From Early Stage to Proof of Concept," European Journal of Pharmaceutical Sciences 31 (2007) 250).

TABLE 1

Solubility definition in the USP

| Description forms (solubility definition) | Parts of solvent required for one part of solute | Solubility range (mg/ml) | Solubility assigned (mg/ml) |
|---|---|---|---|
| Very soluble (VS) | <1 | >1000 | 1000 |
| Freely soluble (FS) | From 1 to 10 | 100-1000 | 100 |
| Soluble | From 10 to 30 | 33-100 | 33 |
| Sparingly soluble (SPS) | From 30 to 100 | 10-33 | 10 |
| Slightly soluble (SS) | From 100 to 1000 | 1-10 | 1 |
| Very slightly soluble (VSS) | From 1000 to 10,000 | 0.1-1 | 0.1 |
| Practically insoluble (PI) | >10,000 | <0.1 | 0.01 |

DETAILED DESCRIPTION

The following description and examples illustrate some embodiments of the disclosed invention in detail. Those of skill in the art will recognize that there are numerous variations and modifications of this invention that are encompassed by its scope. Accordingly, the description of a certain exemplary embodiment should not be deemed to limit the scope of the present invention.

Various embodiments disclose novel classes of multi-arm polyalkylene oxide (e.g., PEG)-based materials including PEGs that are cross-linked or not; formed into nanocarriers, nanogel particles, aggregated nanogel particles, colloidal or coarse dispersions or not; and associated with therapeutic agents, visibility enhancing agents, or not; and having a modified surface structure, or not. In some embodiments, the PEG-based materials can exhibit improved solubility, improved delivery of therapeutic agent, improved delivery or localization of therapeutic, marking or identification agents, or improved delivery and localization of gel material within a body or structure.

There are three primary features of this invention: (1) multi-arm polyalkylene oxide (e.g., PEG) nanocarriers, (2) multi-arm polyalkylene oxide (e.g., PEG) nanogel particle formation in dilute aqueous multi-arm polyalkylene oxide (e.g., PEG) polymer solutions and (3) multi-arm polyalkylene oxide (e.g., PEG) nano- and micro-gel particle formation by aggregation. The invention is particularly useful for agents that require higher amounts, have solubility limitations and/or benefit from targeted delivery to the site of action. Examples of agents include but are not limited to those that may be useful in the treatment or prevention of disease conditions such as asthma, AIDS, or cancer, those that may have utility as imaging compositions, or in aesthetic/cosmetic applications, and more particularly, include agents such as Alexa fluor 790, amprenavir, budesonide, camptothecin, carboplatin, dexamethasone, doxorubicin, Hilyte, Indocyanine green, IRDye, methylprednisolone, paclitaxel, or saquinavir.

Improved delivery of drugs, diagnostics, imaging agents, biological modifiers, and other agents for the diagnosis, mitigation and cure of diseases is highly desirable. A polymeric delivery system has been developed that is potentially useful for local (e.g., breast intraductal, topical), transmucosal (e.g., vaginal, nasal), direct systemic (e.g., intravenous) or oral administration. Multi-arm polyalkylene oxide (e.g., PEG) nanocarriers ranging in size from about 100 Da to about 100,000 Da are the basic building blocks of the multifunctional polymeric agent delivery systems described herein. Nanogel particles may be obtained by intra- and/or inter-molecular crosslinking of multi-arm polyalkylene oxide (e.g., PEG) scaffolds and/or nanocarriers (scaffolds with agents) via formation of disulfide and thioether bonds. Further, stable aggregates of PEG nanogel particles ranging in size from about 10 nm to about 100 nm, (preferably about 20 to about 30 nm) have been formed. Three sizes of aggregated nanogel particles have been produced: about 100 nm and smaller, submicron ANPs (about 100 to about 1000 nm) and microgel ANPs (greater than about 1000 nm to about 1000 microns). The size of particles has been established using Dynamic Light Scattering, Transmission Electron Microscopy and a Coulter Counter. Particles produced in each size range offer distinct advantages for the delivery of a variety of agents including drugs, diagnostics, biological modifiers, imaging agents, etc. For example, after parenteral administration (e.g., intravenous) micron-sized particles travel via the blood and become entrapped in the respective capillary beds of the lungs, liver and spleen (in that order) depending on microparticle size. Submicron nanogels may have utility in the treatment of tumor-based cancers since the pore size of tumor microvessels varies from about 50 to about 1200 nm in diameter. Finally, since the tight junctions between endothelial cells of microvessels are mostly under 2 nm (in general, but up to 10 nm) preferential delivery to, or avoidance of entrance into blood vessels may also be achieved. This is important for applications where maintaining high local and low systemic drug concentrations is a goal. The nanocarriers, nanogel particles or ANPs can be functionalized with a variety of agents to change their body and cell disposition properties. This will ultimately be useful in delivery applications where targeting to and retention in a specific body site or compartment is desired.

PEG or Polyalkylene Oxide Scaffolds

PEG having multiple thiol or thiol reacting groups as well as copolymers of PEG and compounds having thiol groups can be used as scaffolds, or precursors/intermediates for agent delivery systems, nanogel particles, and aggregated nanogel particles and dispersions. PEG scaffolds include polymers containing PEG-thiol groups, polymers containing PEG and peptide thiol groups, copoylmers of PEG and compounds containing thiol groups, and materials including PEG and thiol-reactive groups.

PEG scaffolds, in various embodiments, can be complexed with one or more agents, such as a therapeutic or imaging agents, can be crosslinked with itself or another compound, crosslinked and aggregated, crosslinked and complexed with an agent, or crosslinked and aggregated and complexed with an agent.

Suitable PEG scaffolds include PEG polymers, block polymers, block copolymers and copolymers described below:

PEG Polymers with Thiol Groups—

Materials containing PEG polymer with multiple thiol terminus groups can serve as PEG scaffolds. Suitable materials include PEG having a molecular weight in the range of about 1,000 to about 100,000 Da, with more than 2 thiol groups. Multi-arm PEG and branched PEG are suitable as scaffolds, including multi-arm PEG having 2-, 3-, 4-, or 8-arms, where two or more or even all of the arms have a thiol group. In some embodiments, the thiol group will be unbound, and available for replacement of the hydrogen with another group. In other embodiments, the thiol group can have a different group bound to it that is replaced with a desirable group during complexation, crosslinking, or some combination of the two.

In one preferred embodiment, a multi-arm thiol-terminated PEG nanocarrier such as the 4-arm or 8-arm thiol PEG is presented. The central portion can include a central junction with PEG moieties, linked to the central portion with ether linkages, or other suitable linkages, and terminating in a thiol group for at least some of the PEG moieties.

In some embodiments, multiple thiol groups can be achieved by branching a linear PEG, or by branching a multi-arm PEG, and terminating at least a portion of the branch PEG units with a thiol group. Through branching or a combination of branching and use of multi-arm PEG, the number of thiol groups desired, such as 2, 3, 4, 8, or more can be achieved.

PEG with Peptide Thiol Groups—

The PEG scaffold can include PEG polymer containing multiple units of peptide thiol groups, such as by incorporating multiple cysteine moieties into the structure, either together or separated. Some embodiments can have polycysteine sections incorporated into the structure of the scaffold, such as sections having between about 1 and about 1000 cysteine repeat groups. Certain other embodiments, can have polycysteine sections incorporated into the structure of the scaffold, such as sections having between about 1 and about 24 cysteine repeat groups. Suitable scaffolds can have a molecular weight in the range of about 1,000 to about 100,000 Da.

Copolymer Containing Thiol Groups—

The PEG scaffold can include copolymers of PEG and thiol-containing compounds, such as mercaptosuccinic acid as well as polymers and derivatives of mercaptosuccinic acid. The PEG portion of the copolymer can be functionalized to have thiol or thiol-reactive groups, or not. When the PEG portion is functionalized, the functionalization can occur prior to or after copolymerization. Other suitable copolymerization compounds include peptides having multiple thiol groups, such as contributed by cysteine moieties or provided by functionalizing an amino acid moiety to have a thiol group, or other suitable copolymerization compounds having functional groups suitable for copolymerization with a PEG or functionalized PEG, and providing multiple thiol groups between the PEG portions in the final copolymer.

PEG with Multiple Thiol Reactive Groups—

The PEG scaffold can include PEG with thiol reactive groups which form thiol ether or disulfide bonds when used in combination with, or in place of the thiol groups, as described above. When a thiol reactive group is utilized on the PEG scaffold, a compound used to attach an agent or to crosslink will generally utilize a thiol or activated thiol, vinyl sulfone, maleimide or activated ester to form disulfide, thioether, and thioamide bonds with the scaffold. Suitable thiol reactive groups include those that can be used in conjunction with a thiol-containing compound to attach an agent, or that can react with a thiol group to achieve crosslinking of the PEG scaffold or PEG scaffold with agent. Suitable thiol reactive groups include thiol, activated thiol, vinyl sulfone, maleimide, activated ester and the like. PEG having multiple PEG reactive groups, where the groups are all the same, all different, or a mixture can be utilized, as well as PEG having thiol, activated thiol, vinyl sulfone, maleimide, activated ester and the like PEG or Polyalkylene Oxide Nanocarriers A PEG or polyalkylene oxide nanocarrier can be formed by complexing a PEG or polyalkylene oxide scaffold with a suitable agent. In some embodiments, the complexation is by covalent bond, such as by the formation of a thioether or disulfide bond with the agent or an intermediate, in some embodiments, the complexation can be by non-covalent techniques, such as by ionic bonding, hydrogen bonding, hydrophobic/hydrophillic interaction, van der waals interaction, physical entrapment, etc. Suitable agents include therapeutic agents, such as drugs or other compounds/materials used in the treatment of disease; diagnostic agents, such as those compounds/materials used to identify or evaluate medical conditions or diseases; and imaging agents, such as compounds/materials used in imaging of biological features, such as visually, microscopically, radiographically, electronically, sonographically, photographically etc.

In some embodiments, the PEG or polyalkylene oxide scaffold can have more than one agent molecule complexed to a PEG or polyalkylene oxide scaffold molecule. In some embodiments, there can be 2 or 3 or 4 or 5 or 6 or 7 or 8 or more agent molecules complexed to a PEG or polyalkylene oxide scaffold molecule. In some embodiments, the agent can be attached directly, such as through a covalent bond to the PEG or polyalkylene oxide scaffold. Suitable linkages include thioether, disulfide, thioamide and thiozolidine linkages. In some embodiments, the agent can be attached to the PEG or polyalkylene oxide scaffold through a linking compound, where the linking compound is bonded to both the PEG or polyalkylene oxide scaffold and the agent. Suitable linking compounds include peptides and compounds that have a peptide portion, peptide linkers, enzyme sensitive peptide linkers/linkers, self-immolative linkers, acid sensitive linkers, or bifunctional organic and inorganic crosslinking agents. The linker may be stable or degradable/cleavable. When the drug is doxorubicin, the linker used is Leu-Gly, Glu(Leu-Gly)2, Arg-Gly-Asp-Cys, Gly-Arg-Gly-Asp-Ser, Gly-Arg-Gly-Asp-Ser-Pro, cyclic Arg-Gly-Asp-Tyr-Lys or any peptide with Arg-Gly-Asp.

In some embodiments, the attachment of the agent can favorably modify the functionality of the agent, such as by modifying the solubility, the time release, the stability, the bioavailability, or the targeting of the agent. Some agents, on their own, have only limited solubility in biologically relevant solvents, such as water, water for injection, saline, or buffered saline. Attachment of the agent to PEG or polyalkylene oxide scaffolds to form a nanocarrier can, in some embodiments, result in a higher solubility of the nanocarrier than for the agent alone on a gram/milliliter basis. In some embodiments, the increase in solubility may be sufficient to overcome the increase in molecular weight of the nanocarrier as compared to the agent, and provide a higher soluble dose. When more than one molecule or portion of agent is attached to a nanocarrier, higher agent dosing can be achieved with the same number of grams of nanocarrier as compared to a nanocarrier with only one molecule or portion of agent attached. However, as the amount of agent attached to a nanocarrier increases, the characteristics of the nanocarrier would generally be expected to become more like those of the agent itself, resulting in, for example, a decrease in concentration that can approach the solubility of the agent itself.

In some embodiments, such as in the use of a multi-arm PEG or polyalkylene oxide attached to agents having low solubility, such as an agent that is sparingly or slightly soluble, attachment of additional agents to the PEG or polyalkylene oxide scaffold results in only a limited effect on the solubility of the nanocarrier achieving adequate water solubility and, at the same time, a therapeutically relevant drug dose. In addition bioadhesive targeting can be combined by selection of additional groups to attach to the PEG or polyalkylene oxide scaffold, such as the use of Leu-Gly or Arg-Gly-Asp as a linker for the agent to the PEG or polyalkylene oxide scaffold.

Modification of Surface Charge, Charge Density, and Hydrophobicity

Surface modification is carried out to alter the surface charge, surface charge density, surface hydrophobicity, surface charge and hydrophobicity combined, surface dehesion, body/tissue distribution or intracellular trafficking of NPs and ANPs.

(i) Surface Charge—To modify surface charge, different compounds containing specific side chain groups are reacted to the PEG nanocarrier, nanogel or aggregated nanogels. For example, the reaction of 2-methoxyethanethiol with the scaffold results in a neutral surface charge with an exposed methoxy (OMe) group and the reaction of 1, 2-Ethanedithiol results in a negative surface charge with an exposed —SH group and so on.

(ii) Surface Charge Density—Attaching hydrophobic and hydrophilic amino acids (e.g., Gly, Ala, Asn, Gln, Ser) of various charges to the PEG scaffold of nanogel aggregated particles using a modified citric acid linker double the surface charge density as compared to microparticles prepared in (i) (above).

iii) Surface Hydrophobicity—To increase the hydrophobic surface character, a series of increasingly hydrophobic amino acids (i.e, Gly, Ala, Val, Leu) are covalently linked to the PEG scaffold using mercaptoethanol as the linker. Each of these amino acids has one addition $CH_3$ group adding approximately ½ log unit additional hydrophobicity than the previous amino acid in the series (incremental Hansch $\pi$ value=0.5 per $CH_3$ group).

(iv) Modifying Surface Charge and Hydrophobicity—To modify both the surface charge and hydrophobic interaction, hydrophobic and hydrophilic amino acids (e.g. Gly, Ala, Asn, Gln, Ser) are attached using agents such as mercaptoethanol.

(v) Modifying cell surface adhesion, body/tissue distribution or intracellular trafficking—RGD peptides promote cell binding by interacting with $\alpha_v\beta_3$ intergrins, which are widely expressed on cells. Examples include Arg-Gly-Asp-Cys, Gly-Arg-Gly-Asp-Ser, Gly-Arg-Gly-Asp-Ser-Pro and the cyclic peptide include Arg-Gly-Asp-Tyr-Lys but are not limited to these and can be extended to any peptide having the sequence 'Arg-Gly-Asp'.

Methods for the Measurement of Particle Size.

Particle size is measured using Dynamic Light Scattering (DLS) spectrophotometer. (from 1 nm to 4 micron), b) Particle morphology and size (from 1 nm to ~100 micron) is confirmed using Transmission Electron Microscope (TEM). c) Particle size (from 0.4 nm to 1.2 mm) is measured using a Multisizer™ 3 Coulter Counter using a different aperture tube (Beckman Coulter Corporation, Miami, Fla.) and d) Particle size was measured using Laser Diffraction Particle Size Analyzers (from 400 nm-2 mm).

Detail Procedure:

Particle Size Measurement Using DLS (from 1 nm-4 Micron)

Particle size was measured using a DynaPro 99, Dynamic Light Scattering (DLS) spectrophotometer (Wyatt Technology Corp., Santa Barbara, Calif.). 1 mg of particles were taken in 1.5 mL Eppendorf tube and suspended in 1 mL water by gently shaking by hand for about 30 seconds. 20 µL of the particle suspension was transferred to a cuvette and placed into the instrument. 20 µL of water was used as blank (reference solvent). Readings were taken utilizing a WyattQELS (Quasi-Elastic-Light-Scattering) using a real time digital correaltor instrument at 25° C. in water (acquisition time was 10 seconds, number acquired=20, laser power=100%).

b) Particle Size Measurement Using TEM (from 1 nm-4 Micron)

Particle morphology and size were confirmed using Transmission Electron Microscope (TEM). 1 mg of particles were weighed and put in 1.5 mL Eppendorf tube and suspended in 0.2 mL of water by gently shaking by hand for 30 seconds. 25 µl of particle suspension drop was placed on a 400-mesh carbon coated copper grid. The solution was wicked off the grid and negatively stained with an aqueous solution of 0.5% uranyl acetate. The grids were scoped on a Philips CM12 (FEI, Hillsboro, Oreg.) transmission electron microscope at 80 kV and images were captured with an AMT digital camera.

c) Particle Size Measurement Using Coulter Counter (from 400 nm-1.2 mm)

Particle size was measured using a Multisizer™ 3 Coulter Counter. 1 mg of particles were taken in 1 ml Eppendorf tube and dissolved in 1 ml of water (HPLC grade). 100 µl of particles suspension were mixed and transferred to a Coulter Counter cuvette and cuvette was placed into the instrument. 10 mL Isoton-II was used a blank (reference solvent, Catalog #8546719, Beckman Coulter, Inc., Fullerton, Calif.).

d) Particle Size Measurement Using Laser Diffraction Particle Size Analyzers (from 400 nm-2 mm)

Particle size was measured using in Laser Diffraction particle size analysis (LS 13 320, Beckman Coulter). 100 mg of particles were taken in 1 ml Eppendorf tube and dissolved in 1 ml of water (HPLC grade). 500 µl of particles suspension were mixed and transferred into the instrument.

DETAILED DESCRIPTION OF THE PREFERRED EMBODIMENTS

Example 1

Preparation of PEG-Based Dox Nanocarriers Using Leu-Gly and Glu(Leu-Gly)$_2$

The PEG-based Dox nanocarriers were obtained by a 2-step reaction as described below.

Step 1

N-hydroxy succinimidyl (NHS) glutarate activated PEG polymers were linked (NOF America Corp. White Plains, N.Y., USA) [mPEG$_X$-NHS; X=10 kDa (SUNBRIGHT® ME-100GS), 20 kDa (SUNBRIGHT® ME-200GS), 30 kDa (SUNBRIGHT® ME-300GS), PEG$_X$(NHS)$_2$; X=10 kDa (SUNBRIGHT® DE-100GS), 20 kDa (SUNBRIGHT® DE-200GS), and PEG$_X$(NHS)$_4$; X=10 kDa (SUNBRIGHT® PTE-100GS), 20 kDa (SUNBRIGHT® PTE-200GS)] to amino terminus of either Leu-Gly (LG; MW=188; Catalog No. L9625, Sigma-Aldrich Corp., St. Louis, Mo., USA) or Glu(Leu-Gly)$_2$ (E[LG]$_2$; MW=487; custom synthesized by EZBiolab Inc., Carmel, Ind., USA) in sodium carbonate buffer (pH 8.4) to obtain PEGylated peptides {mPEG$_X$-Leu-Gly (X=10, 20, 30 kDa), mPEG$_X$-Glu(Leu-Gly)$_2$ (X=10, 20 kDa), PEG$_X$(Leu-Gly)$_2$ (X=10, 20 kDa), PEG$_X$[Glu(Leu-Gly)$_2$]$_2$ (X=10, 20 kDa), PEG$_X$(Leu-Gly)$_4$ (X=10, 20 kDa), PEG$_X$[Glu(Leu-Gly)$_2$]$_4$ (X=10, 20 kDa)} with amide linkages (Table 2).

Step 2

The carboxyl terminus of PEGylated peptides was linked {mPEG$_X$-Leu-Gly (X=10, 20, 30 kDa), mPEG$_X$-Glu(Leu-Gly)$_2$ (X=10, 20 kDa), PEG$_X$(Leu-Gly)$_2$ (X=10, 20 kDa), PEG$_X$[Glu(Leu-Gly)$_2$]$_2$ (X=10, 20 kDa), PEG$_X$(Leu-Gly)$_4$ (X=10, 20 kDa), PEG$_X$[Glu(Leu-Gly)$_2$]$_4$ (X=10, 20 kDa)} to amino terminus of Doxorubicin hydrochloride (Dox.HCl; MW=580; custom synthesized by Changsha Huajia, China) in presence of benzotriazol-1-yl-oxytripyrrolidinophosphonium hexafluorophosphate (PyBOP; MW=520.3; Catalog No. 01-62-0016, Novabiochem Corp., San Diego, Calif.), N-hydroxybenzotriazole (HOBt; MW=135.1; Catalog No. 01-62-0008, Novabiochem Corp., San Diego, Calif.), N,N'-diisopropylethylamine (DIEA; Catalog No. 230-392-0, Acros Organics, Geel, Belgium) and N,N-dimethylformamide (DMF; Catalog No. 68-12-2, Acros Organics, Morris Plains, N.J.) to obtain PEGylated Dox nanocarriers {mPEG$_X$-Leu-Gly-Dox (X=10, 20, 30 kDa, 1 copy Dox), mPEG$_X$-Glu(Leu-Gly-Dox)$_2$ (X=10, 20 kDa, 2 copy Dox), PEG$_X$(Leu-Gly-Dox)$_2$ (X=10, 20 kDa, 2 copy Dox), PEG$_X$[Glu(Leu-Gly-Dox)$_2$]$_2$ (X=10, 20 kDa, 4 copy Dox), PEG$_X$(Leu-Gly-Dox)$_4$ (X=10, 20 kDa, 4 copy Dox), PEG$_X$[Glu(Leu-Gly-Dox)$_2$]$_4$ (X=10, 20 kDa, 8 copy Dox)} with amide linkages (Table 2).

Example 1A

Preparation of PEG$_{20kDa}$[Glu(Leu-Gly-Dox)$_2$]$_2$ (4 Copy Dox)

Step 1
Preparation of Sodium Carbonate Buffer

A solution of 0.1 M sodium carbonate buffer was prepared by mixing 8 ml of 0.2M sodium carbonate (Na$_2$CO$_3$; MW=106.0; Catalog No. S-2127, Sigma-Aldrich Corp., St. Louis, Mo., USA) [obtained by dissolving 2.12 g of Na$_2$CO$_3$ in 100 ml of D.I. HPLC grade water] with 17 ml of 0.2M sodium bicarbonate (NaHCO$_3$; MW=84.0; Catalog No. BP328-1, Fisher Scientific, Pittsburgh, Pa.) [obtained by dissolving 1.68 g of NaHCO$_3$ in 100 ml of D.I. HPLC grade water]. The pH was then adjusted to pH 8.4 with 0.1 N hydrochloric acid (HCl). Unless otherwise indicated, all further references to sodium carbonate buffer refer to 0.1 M pH 8.4, prepared in this manner. Likewise, unless otherwise indicated, all references to water refer to D.I. HPLC grade water.

Preparation of PEG Polymer [PEG$_{20kDa}$(NHS)$_2$] Solution 1.0 g (1 equiv.) of PEG$_{20kDa}$(NHS)$_2$ (MW=20,000; SUNBRIGHT® DE-200GS; NOF America Corp., White Plains, N.Y., USA) was weighed (Balance: Sartorius CP64) in a 50 ml Greiner centrifuge tube. 8.0 ml of sodium carbonate buffer was added to dissolve the PEG polymer.

Preparation of Peptide (Glu[Leu-Gly]$_2$) Solution 200 mg (8 equiv.) of Glu[Leu-Gly]$_2$ (MW=487; custom synthesized by EZBiolab Inc., Carmel, Ind., USA) was weighed (Balance: Sartorius CP64) in a 15 ml Greiner centrifuge tube. 1.5 ml of sodium carbonate buffer was added to dissolve the peptide.

Preparation of PEGylated Peptide {PEG$_{20kDa}$[Glu(Leu-Gly)$_2$]$_2$}

The PEG polymer solution was mixed with the peptide solution and the reaction mixture was stirred (speed 1800 rpm) on a magnetic stirrer (Corning model PC 310, Kent City, Mich.) at room temperature (24° C.) for 12 hours. The crude PEGylated peptide product was subjected to gel permeation chromatography performed on Sephadex G-50 (Amersham Bioscience, Uppsala, Sweden) using water as eluent. The fractions corresponding to purified PEGylated peptide product were pooled and lyophilized (Labconco, FreeZone 2.5 plus, temperature: −84° C.; pressure: 0.010 millibar), yielding PEGylated peptide as a white solid. Yield (%)=85.

Analysis of PEG Polymer [PEG$_{20kDa}$(NHS)$_2$] and PEGylated Peptide {PEG$_{20kDa}$[Glu(Leu-Gly)$_2$]$_2$}

The PEG polymer and the purified PEGylated peptide was analyzed using Matrix-assisted-laser-desorption-ionization-time-of-flight mass spectrometry [MALDI-TOF/TOF (ABI-MDS SCIEX 4800)]. 1 mg of PEGylated peptide was taken in 1.5 ml Eppendorf tube and dissolved in 1 ml of water by gently shaking by hand for about 30 seconds. 5 μl of this PEGylated peptide solution was mixed with 24 μl matrix (sinnapinic acid) solution. 1.5 μl of the PEGylated peptide-matrix was spotted on a 384 well MALDI sample plate and placed into the instrument. The PEG polymer was also prepared, spotted and analyzed in the same manner. The PEG polymer and the PEGylated peptide molecular weights were found to be 20,829 Da (FIG. 1) and 21,786 Da (FIG. 2) respectively. The MW corresponding to 21,786 Da confirms that 2 copies of Glu(Leu-Gly)$_2$ peptide were attached to the PEG polymer, thus confirming the product to be PEG$_{20kDa}$[Glu(Leu-Gly)$_2$]$_2$.

Step 2
Preparation of PEGylated Peptide {PEG$_{20kDa}$[Glu(Leu-Gly)$_2$]$_2$)} Solution mg (1 equiv.) of PEGylated peptide was weighed (Balance ID=Sartorius CP64) in a 15 ml Greiner centrifuge tube. 1.0 ml of N,N-dimethylformamide (DMF; Catalog No. 68-12-2, Acros Organics, Morris Plains, N.J.) was added to dissolve the PEGylated peptide. The PEGylated peptide solution was activated using 24 mg (21 equiv.) of benzotriazol-1-yl-oxytripyrrolidinophosphonium hexafluorophosphate (PyBOP; MW=520.3; Catalog No. 01-62-0016, Novabiochem Corp., San Diego, Calif.) and 6 mg (21 equiv.) of N-hydroxybenzotriazole (HOBt; MW=135.1; Catalog No. 01-62-0008, Novabiochem Corp., San Diego, Calif.) both solutions prepared in 1.0 ml of DMF.

Preparation of Doxorubicin Solution 20 mg (7 equiv.) of doxorubicin hydrochloride (Dox.HCl; custom synthesized by Changsha Huajia, China) was weighed (Balance: Sartorius CP64) in a 15 ml Greiner centrifuge tube. 5.0 ml of DMF was added to dissolve the Dox. 10 μl (21 equiv.) of N,N'-diisopropylethylamine (DIEA, Catalog No. 230-392-0, Acros Organics, Geel, Belgium) was added to make the Dox solution slightly basic.

Preparation of PEGylated Dox {PEG$_{20kDa}$[Glu(Leu-Gly-Dox)$_2$]$_2$ (4 Copy Dox)}

The PEGylated peptide solution was mixed with the Dox solution and the reaction mixture was stirred (speed 1800 rpm) on a magnetic stirrer (Corning model PC 310, Kent City, Mich.) at room temperature (24° C.) for 12 hours. The crude PEGylated Dox product was subjected to gel permeation chromatography performed on Sephadex G-50 (Amersham Bioscience, Uppsala, Sweden) using water as eluent. The fractions corresponding to purified PEGylated Dox product were pooled and lyophilized (Labconco, FreeZone 2.5 plus, temperature: −84° C.; pressure: 0.010 millibar), yielding PEGylated Dox as a reddish orange solid. Yield (%)=60.

Analysis of PEGylated Dox {$PEG_{20kDa}$[Glu(Leu-Gly-Dox)$_2$]$_2$ (4 Copy Dox)}

The purified PEGylated Dox was analyzed using Matrix-assisted-laser-desorption-ionization-time-of-flight mass spectrometry [MALDI-TOF/TOF (ABI-MDS SCIEX 4800)]. 1 mg of PEGylated Dox was taken in 1.5 ml Eppendorf tube and dissolved in 1 ml of water by gently shaking by hand for about 30 seconds. 5 μl of this PEGylated Dox solution was mixed with 24 μl matrix (sinnapinic acid) solution. 1.5 μl of the PEGylated Dox-matrix was spotted on a 384 well MALDI sample plate and placed into the instrument. The MW corresponding to 23,090 Da (FIG. 3) confirms that 4 copies of Dox were attached to the PEGylated peptide, thus confirming the product to be $PEG_{20kDa}$[Glu(Leu-Gly-Dox)$_2$]$_2$ with a total Dox content of 9.6 wt %.

Solubility Testing of PEGylated Dox {$PEG_{20kDa}$[Glu(Leu-Gly-Dox)$_2$]$_2$ (4 Copy Dox)} in Water The aqueous solubility of the PEGylated Dox nanocarrier was tested at room temperature (24° C.) by weighing 30 mg of lyophilized (Labconco, FreeZone 2.5 plus, temperature: −84° C.; pressure: 0.010 millibar) PEGylated Dox {$PEG_{20kDa}$[Glu(Leu-Gly-Dox)$_2$]$_2$ (4 copy Dox)} (Balance: Sartorius CP64) in a 15 ml Greiner centrifuge. To this dried nanocarrier was added D.I. HPLC grade water in small parts by gently shaking by hand for about 30 seconds until the nanocarrier was completely dissolved. A total of 0.25 ml D.I. HPLC grade water was needed to dissolve the 30 mg of PEGylated Dox nanocarrier. Thus, the solubility of the nanocarrier was found to be 120 mg/ml, which is termed "freely soluble" according to the USP solubility criterion ("freely soluble" range=100-1000 mg/ml). This nanocarrier is about 12 times more soluble than non-conjugated Dox (solubility of Doxorubicin Hydrochloride in water=~10 mg/ml)

Dox Loading Capacity of PEGylated Dox {$PEG_{20kDa}$[Glu(Leu-Gly-Dox)$_2$]$_2$ (4 copy Dox)} in "Freely Soluble" Range The PEGylated Dox nanocarrier with a solubility limit of 120 mg/ml corresponding to $PEG_{20kDa}$[Glu(Leu-Gly-Dox)$_2$]$_2$ (4 copy Dox) possess a Dox loading capacity of 11.5 mg/ml which is about 5.8 times higher as compared to marketed Dox products (2 mg/ml in case of both Doxil and Doxorubicin Hydrochloride products). Therefore, in order to match the marketed Dox dose of 2 mg/ml, the amount of the synthesized PEGylated Dox nanocarrier required is about 20.9 mg/ml of $PEG_{20kDa}$[Glu(Leu-Gly-Dox)$_2$]$_2$ (4 copy Dox), which is well below the "freely soluble" range.

TABLE 2

Parameters used for the preparation of doxorubicin (Dox) nanocarriers using peptide (Leu-Gly, LG) and peptide (Glu[Leu-Gly]$_2$, E[LG]$_2$) linkers

| Poly(ethylene glycol) (PEG) (MW, shape) | LG (copy number) | E(LG)$_2$ (copy number) | Dox (copy number) | Dox nanocarrier |
|---|---|---|---|---|
| mPEG$_{5\,kDa}$-NHS | 1 | — | 1 | mPEG-LG-Dox |
| mPEG$_{10\,kDa}$-NHS | 1 | — | 1 | mPEG-LG-Dox |
| mPEG$_{20\,kDa}$-NHS | 1 | — | 1 | mPEG-LG-Dox |
| mPEG$_{30\,kDa}$-NHS | 1 | — | 1 | mPEG-LG-Dox |
| mPEG$_{20\,kDa}$-NHS | — | 1 | 2 | mPEG-E(LG-Dox)$_2$ |
| PEG$_{20\,kDa}$(NHS)$_2$ | 2 | — | 2 | PEG(LG-Dox)$_2$ |
| PEG$_{20\,kDa}$(NHS)$_2$ | — | 2 | 4 | PEG[E(LG-Dox)$_2$]$_2$ |
| PEG$_{10\,kDa}$(NHS)$_4$ | — | 4 | 8 | PEG[E(LG-Dox)$_2$]$_4$ |
| PEG$_{20\,kDa}$(NHS)$_4$ | 4 | — | 4 | PEG(LG-Dox)$_4$ |
| PEG$_{20\,kDa}$(NHS)$_4$ | — | 4 | 8 | PEG[E(LG-Dox)$_2$]$_4$ |

Constant parameters: solvent: $Na_2CO_3$ buffer pH 8.4/DMF, coupling agents-PyBOP/HOBt/DIEA. Similar procedures were used for the preparation of other PEG-Dox nanocarriers using either Leu-Gly or Glu(Leu-Gly)$_2$ peptides and PEG polymers as mentioned in Table 2.

Example 2

Preparation of PEG-Based Dox Nanocarriers Using Bioadhesive Peptide, Arg-Gly-Asp-Cys (RGDC)

The PEG-based RGDC-Dox nanocarriers were obtained by 2-step reaction as described below.

Step 1

The amino terminus of doxorubicin hydrochloride was linked (Dox.HCl; MW=580; custom synthesized by Changsha Huajia, China) to carboxy terminus of Arg-Gly-Asp-Cys (RGDC; MW=447.5; custom synthesized by American Peptide Company Inc. Sunnyvale, Calif.) in the presence of diisopropylcarbodiimide (DIPC; MW=126.2; Catalog No. D-125407, Sigma Aldrich Corp., St. Louis, Mo., USA), N-hydroxybenzotriazole (HOBt; MW=135.1; Catalog No. 01-62-0008, Novabiochem Corp., San Diego, Calif.), 4-methyl morpholine (MMP; MW=101.1; Catalog No. M-56557, Sigma Aldrich Corp., St. Louis, Mo., USA) and N,N-dimethylformamide (DMF; Catalog No. 68-12-2, Acros Organics, Morris Plains, N.J.) to obtain Dox-peptide (RGDC-Dox) with amide linkage (Table 3).

Step 2

N-hydroxy succinimidyl (NHS) glutarate activated PEG polymers were linked (NOF America Corp., White Plains, N.Y., USA) {$PEG_X$(NHS)$_4$; X=20 kDa (SUNBRIGHT® PTE-200GS), 40 kDa (SUNBRIGHT® PTE-400GS), $PEG_X$(NHS)$_8$; X=20 kDa (SUNBRIGHT® HGEO-200GS)} to amino terminus of RGDC-Dox in phosphate buffer (pH 7.4) to obtain PEGylated Dox nanocarriers {$PEG_X$(RGDC-Dox)$_4$, (X=20, 40 kDa, 4 copy Dox) and $PEG_X$(RGDC-Dox)$_8$ (X=20 kDa, 8 copy Dox)} with amide linkages (Table 3).

Example 2A

Preparation of $PEG_{20kDa}$(RGDC-Dox)$_4$ (4 Copy Dox)

Step 1

Preparation of Phosphate Buffer (PB)

A solution of 1.0 M sodium phosphate dibasic ($Na_2HPO4$; Catalog No. S-9763, Sigma Aldrich Corp., St. Louis, Mo.) was prepared in a volumetric flask by dissolving 14.2 grams of salt in 100 ml of deionized (D.I.) HPLC grade water. Similarly, the solution of 1.0 M sodium phosphate monobasic ($NaH_2PO4$; Catalog No. S-0751, Sigma Aldrich Corp., St. Louis, Mo., USA) was prepared in another flask by dissolving 12.0 grams of salt in 100 ml D.I. HPLC grade water. A solution of 0.1 M phosphate buffer (PB) was prepared by mixing 7.7 ml of sodium phosphate dibasic solution with 2.3 ml of sodium phosphate monobasic solution in a beaker. D.I. HPLC water (80.0 mL) was then added to the beaker and the pH of the solution was measured at room temperature (25° C.) on a pH meter (Symphony SB70P, VWR International, Pittsburgh, Pa.). The solution was stirred gently (<500 rpm/min) while measuring the pH and the pH value was adjusted to 7.4 using 0.1N sodium hydroxide solution (NaOH; Catalog No. SS276-4, Fisher Scientific, Suwanee, Ga.). Finally, the buffer was transferred to a volumetric flask and D.I. HPLC water was added to adjust the final buffer volume to 100 ml. The buffer was stored at 4° C. and brought to room temperature prior to use. Unless otherwise indicated, all further references to phosphate buffer (PB) in example 2 refers to 0.1 M pH 7.4, prepared in this manner. Likewise, unless otherwise indicated, all references to water refer to D.I. HPLC grade water.

Preparation of Peptide (Arg-Gly-Asp-Cys; RGDC) Solution 40 mg (1 equiv.) of RGDC (MW=447.5; custom synthesized by American Peptide Company Inc. Sunnyvale, Calif., USA) was weighed (Balance: Sartorius CP64) in a 15 ml Greiner centrifuge tube. 1.5 ml of N,N-dimethylformamide (DMF; Catalog No. 68-12-2, Acros Organics, Morris Plains, N.J.) was added to dissolve the peptide. To this peptide solution was added 8.7 mg (1 equiv.) of diisopropylcarbodiimide (DIPC; MW=126.2; Catalog No. D-125407, Sigma Aldrich Corp., St. Louis, Mo., USA) and 36 mg (4 equiv.) of N-hydroxybenzotriazole (HOBt; MW=135.1; Catalog No. 01-62-0008, Novabiochem Corp. San Diego, Calif.).

Preparation of Doxorubicin (Dox) Solution 40 mg (1 equiv.) of doxorubicin hydrochloride (Dox.HCl; custom synthesized by Changsha Huajia, China) was weighed (Balance: Sartorius CP64) in a 15 ml Greiner centrifuge tube. 1.5 ml of DMF was added to dissolve the Dox. To this Dox solution was added 28 mg (4 equiv.) of 4-methyl morpholine (MMP; MW=101.1; Catalog No. M-56557, Sigma Aldrich Corp., St. Louis, Mo., USA).

Preparation of Dox Peptide [RGDC-Dox]

The peptide solution was mixed with the Dox solution and the reaction mixture was stirred (speed 1800 rpm) on a magnetic stirrer (Corning model PC 310, Kent City, Mich.) at room temperature (24° C.) for 12 hours. The Dox peptide product was dissolved in water and lyophilized (Labconco, FreeZone 2.5 plus, temperature: −84° C.; pressure: 0.010 millibar) to obtain a red powder. Yield (%) ~90.

Step 2

Preparation of Dox-Peptide [RGDC-Dox] Solution 35 mg (1.5 equiv.) of RGDC-Dox was weighed (Balance: Sartorius CP64) in a 50 ml Greiner centrifuge tube. 3.0 ml of phosphate buffer was added to dissolve the Dox peptide.

Preparation of PEG Polymer [$PEG_{20kDa}(NHS)_4$] Solution 462 mg (1 equiv.) of $PEG_{20kDa}(NHS)_4$ (MW=20,000; SUNBRIGHT® PTE-200GS; NOF America Corp. White Plains, N.Y., USA) was weighed (Balance: Sartorius CP64) in a 50 ml Greiner centrifuge tube. 5.0 ml phosphate buffer was added to dissolve the PEG polymer.

Preparation of PEGylated Dox-Peptide {$PEG_{20kDa}$(RGDC-Dox)$_4$ (4 Copy Dox)}

The PEG polymer solution was mixed with the Dox-peptide solution and the reaction mixture was stirred (speed 1800 rpm) on a magnetic stirrer (Corning model PC 310, Kent City, Mich.) at room temperature (24° C.) for 12 hours. The crude PEGylated Dox-peptide product was subjected to gel permeation chromatography performed on Sephadex G-50 (Amersham Bioscience; Uppsala, Sweden) using water as eluent. The fractions corresponding to purified PEGylated Dox-peptide product were pooled and lyophilized (Labconco, FreeZone 2.5 plus, temperature: −84° C.; pressure: 0.010 millibar), yielding PEGylated Dox-peptide as a reddish orange solid. Yield (%)=70.

Analysis of PEGylated Dox-Peptide {$PEG_{20kDa}$(RGDC-Dox)$_4$ (4 Copy Dox)}

The purified PEGylated Dox-peptide was analyzed using Matrix-assisted-laser-desorption-ionization-time-of-flight mass spectrometry [MALDI-TOF/TOF (ABI-MDS SCIEX 4800)]. 1 mg of PEGylated Dox-peptide was taken in 1.5 ml Eppendorf tube and dissolved in 1 ml water by gently shaking by hand for about 30 seconds. 5 μl of this PEGylated Dox-peptide solution was mixed with 24 μl matrix (sinnapinic acid) solution. 1.5 μl of the PEGylated Dox-peptide-matrix was spotted on a 384 well MALDI Sample Plate and placed into the instrument. The PEG polymer was also prepared, spotted and analyzed in the same manner. The PEG polymer and the PEGylated Dox-peptide molecular weights were found to be 21,451 Da (FIG. 4) and 24,812 Da (FIG. 5) respectively. The MW corresponding to 24,812 Da confirms that 4 copies of Dox-peptide were attached to the PEG polymer confirming the product to be $PEG_{20kDa}$(RGDC-Dox)$_4$. The purified PEGylated Dox-peptide was also analyzed using size-exclusion-chromatography (SEC)/High-performance-liquid-chromatography (HPLC) [Breeze GPC System] with a SEC column (Water Ultrahydrogel 1000). 1 mg of PEGylated Dox-peptide was taken in 1.5 ml Eppendorf tube and dissolved in 1 ml of water by gently shaking by hand for about 30 seconds. 25 μl of this PEGylated Dox-peptide solution was injected into the instrument. D.I. HPLC grade water was used as the mobile phase with a flow rate of 1 ml/min. The PEG polymer was also prepared and analyzed in the same manner. The PEG polymer and the PEGylated Dox-peptide retention times were found to be ~10 min (FIG. 6) and ~7 min (FIG. 8) respectively using a refractive index (RI) detector. The higher retention time corresponding to ~7 min confirmed that Dox-peptide was attached to the PEG polymer confirming the product to be $PEG_{20kDa}$(RGDC-Dox)$_4$. This product, $PEG_{20kDa}$(RGDC-Dox)$_4$ was also visualized with a Ultra-Violet (UV) detector at 254 nm at a retention time of ~7 min (FIG. 9) whereas the corresponding unconjugated PEG polymer, $PEG_{20kDa}$(NHS)$_4$ showed no peak at 254 nm (FIG. 7) showing the absence of Dox-peptide.

Solubility Testing of PEGylated Dox-Peptide {$PEG_{20kDa}$(RGDC-Dox)$_4$ (4 Copy Dox)} in Water The aqueous solubility of the PEGylated Dox-peptide nanocarrier was tested at room temperature (24° C.) by weighing 12.5 mg of lyophilized (Labconco, FreeZone 2.5 plus, temperature: −84° C.; pressure: 0.010 millibar) PEGylated Dox-peptide {$PEG_{20kDa}$(RGDC-Dox)$_4$ (4 copy Dox)} (Balance: Sartorius CP64) in a 15 ml Greiner centrifuge. To this dried nanocarrier was added D.I. HPLC grade water in small parts by gently shaking by hand for about 30 seconds until the nanocarrier was completely dissolved. A total of 0.1 ml D.I. HPLC grade water was needed to dissolve the 12.5 mg of PEGylated Dox-peptide nanocarrier. Thus, the solubility of the nanocarrier was found to be 125 mg/ml, which is termed "freely soluble" according to the USP solubility definition ("freely soluble" range=100-1000 mg/ml). This nanocarrier is about 13 times more soluble than non-conjugated Dox (solubility of Doxorubicin Hydrochloride in water: ~10 mg/ml).

Dox Loading Capacity of PEGylated Dox-Peptide {PEG$_{20kDa}$(RGDC-Dox)$_4$ (4 Copy Dox)} in "Freely Soluble" Range The PEGylated Dox-peptide nanocarrier with a solubility limit of 125 mg/ml corresponding to PEG$_{20kDa}$(RGDC-Dox)$_4$ (4 copy Dox) possess a Dox loading capacity of 11.9 mg/ml which is about 6 times higher as compared to marketed Dox products (2 mg/ml in case of both Doxil and Doxorubicin Hydrochloride). Therefore, in order to match the marketed Dox dose of 2 mg/ml, the amount of the synthesized PEGylated Dox-peptide nanocarrier required is about 21.0 mg/ml of PEG$_{20kDa}$(RGDC-Dox)$_4$ (4 copy Dox) which is well below the "freely soluble" range.

TABLE 3

Parameters used for the preparation of doxorubicin (Dox) nanocarriers using a bioadhesive peptide (Arg-Gly-Asp-Cys, RGDC) linker

| Poly(ethylene glycol) (PEG) (MW, shape) | RGDC (copy number) | Aldrithiol (TP-TP) (copy number) | SPDP (copy number) | Dox (copy number) | Dox nanocarrier |
|---|---|---|---|---|---|
| 8-arm 20 kDa PEG(SH)$_8$ | 8 | 8 | — | 8 | PEG[S-S-C(Dox)DGR]$_8$ |
| 4-arm 20 kDa PEG(SH)$_4$ | 4 | 4 | — | 4 | PEG[S-S-C(Dox)DGR]$_4$ |
| 8-arm 20 kDa PEG(NHS)$_8$ | 8 | — | — | 8 | PEG[RGDC-Dox]$_8$ |
| 4-arm 20 kDa PEG(NHS)$_4$ | 4 | — | — | 4 | PEG[RGDC-Dox]$_4$ |
| 4-arm 20 kDa PEG(NHS)$_4$ | 4 | — | 4 | 8 | PEG[RGDC(S-S-Dox)Dox]$_4$ |
| 4-arm 40 kDa PEG(NHS)$_4$ | 4 | — | — | 4 | PEG[RGDC-Dox]$_4$ |

Constant parameters: solvent-DMF/PB pH 7.4, coupling agents-DIPC/HOBt/MMP. Similar procedures were used for the preparation of other PEGylated RGDC-Dox nanocarriers using PEG polymers as mentioned in Table 3.

Example 3A

Preparation of PEG$_{20kDa}$-NHCO-fluorescein Nanocarrier

Preparation of Sodium Phosphate Buffer (0.1 M, pH 7.94±0.05)

A solution of sodium phosphate dibasic (0.5 M, Catalog # S-9763, Sigma Aldrich, St. Louis, Mo.) was prepared in a volumetric flask by dissolving 7.09 grams of salt in 100.0 mL of deionized (DI) water. Similarly, the solution of sodium phosphate monobasic (0.5 M, Catalog # S-0751, Sigma Aldrich, St. Louis, Mo.) was prepared in another flask by dissolving 6.00 grams of salt in 100.0 mL DI water. 75.66 mL of sodium phosphate dibasic solution was transferred to a beaker and 5.44 ml of sodium phosphate monobasic solution was added to it. DI water (300.0 mL) was added to the beaker and pH of the solution was measured at room temperature (24° C.) on a pH meter (Symphony SB70P, VWR International, Pittsburgh, Pa.). The solution was stirred gently (<500 rpm/min) while measuring the pH and pH was estimated as 7.94. Buffer was transferred to a volumetric flask and DI water was added to adjust the final buffer volume to 400.0 mL. The buffer was stored at 4° C. and brought to room temperature prior to use. Unless otherwise indicated, all reference to DI refers to deionized water. Likewise, unless otherwise indicated, all reference to PB in this example 3A refers to 0.1 M phosphate buffer, pH, 7.94.

Preparation of Nanocarrier

The amine functionalized poly(ethylene glycol) polymer (PEG$_{20kDa}$-NH$_2$, 100 mg, 4.6×10$^{-3}$ mM; Catalog # SUN-BRIGHT MEPA-20T, NOF America Corporation, White Plains, N.Y.) was weighed in a 50 mL centrifuge tube and PB (10.0 mL) was added. The mixture was gently stirred (1000 rpm) at room temperature (24° C.) to make a clear solution, and 5-carboxyfluorescein succinimidyl ester (5 equiv., 11.08 mg; Catalog #81007, Anaspec, San Jose, Calif.) was added next. The centrifuge tube containing the reaction mixture was covered with aluminum foil (for dark conditions) and the reaction mixture was stirred (1000-1500 rpm) at room temperature (24° C.) for overnight period (~12 hours). After 12 hours, the stirring was stopped.

Purification of Nanocarrier

Nanocarrier was purified by gel-permeation chromatography (GPC) on Sephadex G50 column in dark using DI water as eluent. Prior to use, Sephadex G50 medium gel filtration media (Catalog #17.0043-01, VWR International, Pittsburgh, Pa.) was soaked in DI water (25 mg/500 mL) at room temperature (25° C.) for 24 hours. The presoaked Sephadex was loaded on to the Kontes GPC column (Catalog # KT420400-1550, VWR International, Pittsburgh, Pa.; internal diameter: 2.5 cm; length: 50 cm, Sephadex column length: 40 cm). Reaction mixture (10×1.0 mL) was loaded onto the column and eluted using DI water; the high molecular weight nanocarrier eluted first followed by low molecular weight fluorescein. High molecular weight fractions were pooled together and lyophilized for 5-days (Labconco, FreeZone 2.5 plus, temperature: −84° C.; pressure: 0.010 millibar). Nanocarrier was obtained as yellow flakes (66.9 mg).

Characterization of Nanocarrier

Nanocarrier was characterized on Waters Breeze GPC system (Waters Corporation, Milford, Mass.) equipped with 2487 dual-wavelength UV (absorption wavelength set to 220 and 480 nm) and 2414 refractive index detectors. DI water was used as mobile phase at a flow rate of 1.0 mL minute$^{-1}$ and analyses was performed on Waters Ultrahydrogel 1000 GPC column (7.8×300 mm, Catalog # WAT011535, Waters Corporation, Milford, Mass.), run time: 30 minutes. The polymer and nanocarrier solutions were prepared by dissolving the sample (2.0 mg) in DI water (1.0 mL) and injected (200.0 μL) into the system. The unmodified polymer showed retention time of 8.3 minutes whereas the nanocarrier showed the retention time of 7.2 minutes. The unmodified polymer showed a peak in refractive index panel but not the UV panel because PEG does not absorb at 480 nm, however, nanocarrier showed peak in UV panel too due to the presence of fluorescein, which strongly absorbs at 480 nm wavelengths.

Different nanocarrier examples are summarized in Table 4A.

TABLE 4A

| Nanocarrier | Polymer | Dye | Yield (mg) |
|---|---|---|---|
| $PEG_{20\ kDa}$-NHCO-fluorescein* | $PEG_{20\ kDa}$-$NH_2$ | 5-carboxyfluorescein succinimidyl ester | 66.9 |
| $PEG_{12\ kDa}$-NHCO-fluorescein* | $PEG_{12\ kDa}$-$NH_2$ | 5-carboxyfluorescein succinimidyl ester | 79.9 |
| $PEG_{30\ kDa}$-NHCO-fluorescein* | $PEG_{30\ kDa}$-$NH_2$ | 5-carboxyfluorescein succinimidyl ester | 74.3 |
| $PEG_{40\ kDa}$-NHCO-fluorescein* | $PEG_{40\ kDa}$-$NH_2$ | 5-carboxyfluorescein succinimidyl ester | 72.0 |
| $PEG_{60\ kDa}$-NHCO-fluorescein* | $PEG_{60\ kDa}$-$NH_2$ | 5-carboxyfluorescein succinimidyl ester | 65.8 |
| $PEG_{20\ kDa}$-NHCO-methyle blue* | $PEG_{20\ kDa}$-$NH_2$ | Methylene blue, carboxylic acid succinimidyl ester | 84.7 |
| $PEG_{20\ kDa}$-[NHCO-fluorescein]$_4$ | $PEG_{20\ kDa}$-[$NH_2$]$_4$ | 5-carboxyfluorescein succinimidyl ester | 79.8 |
| $PEG_{20\ kDa}$-[NHCO-methylene blue]$_4$ | $PEG_{20\ kDa}$-[$NH_2$]$_4$ | Methylene blue, carboxylic acid succinimidyl ester | 58.2 |

*Nanocarriers prepared using the procedure described in example 3A. All polymers were obtained from NOF America Corporation (Catalog # SUNBRIGHT MEPA20T, MEPA-12T, MEPA-30T, MEPA-40T, GL2600MA, PTE-200PA; White Plains, NY) and methylene blue derivative was obtained from Biosearch Technologies, Novato, CA (Catalog # MB-1000S).

Example 3B

Preparation of Hydrogel with Passively Entrapped $PEG_{60kDa}$-NHCO-fluorescein Nanocarrier Preparation of Sodium Phosphate Buffer (0.02 M, pH=7.44±0.05)

Sodium phosphate dibasic (1 M, Catalog # S-9763, Sigma Aldrich, St. Louis, Mo.) and monobasic (1 M, Catalog # S-0751, Sigma Aldrich, St. Louis, Mo.) solutions were prepared separately in volumetric flasks. 1.54 mL of sodium phosphate dibasic and 0.46 mL of sodium phosphate monobasic solutions were transferred to a beaker and 80.0 mL of DI water was added to it. The pH of buffer was measured as described in example 3A and pH value was adjusted to 7.44 using 0.1 N sodium hydroxide solution (Catalog # SS276-4, Fisher Scientific, Suwanee, Ga.). The solution was transferred to a volumetric flask and more DI water was added to adjust the final volume to 100 mL. Unless otherwise indicated, all reference to DI refers to deionized water. Likewise, unless otherwise indicated, all reference to PB in example 3B refers to 0.02 M phosphate buffer, pH, 7.44.

Preparation of Polymer Solution Containing the Nanocarrier

Eight-arm $PEG_{20kDa}$[SH]$_8$ (6 mg, 3×10$^{-4}$ mM, Catalog # SUNBRIGHT HGEO-200SH, NOF America Corporation, White Plains, N.Y.) was weighed in a centrifuge tube and dissolved in PB (80 μL). The $PEG_{60kDa}$-NHCO-fluorescein nanocarrier was weighed and mixed into the polymer solution (1 mg, 1.6×10$^{-5}$ mM) by vortexing for <1 minutes.

Preparation of Crosslinker Solution

Crosslinker solution was prepared by weighing 1.28 mg of 1,6-Hexane-bis-vinylsulfone (HBVS, MW=266.38, Catalog #22334, Pierce Protein Research Products, Thermo Fisher Scientific, Rockford, Ill.) in a centrifuge tube. PB (80 μL) was added to the centrifuge tube and the mixture was gently heated (50-60° C.) for 2-3 minutes followed by vortexing for 2-3 minutes to dissolve the crosslinker into the buffer solution. The solution was allowed to come to the room temperature; 20 μL of this solution (0.32 mg, 4 equiv., 1.2×10$^{-3}$ mM) was used for hydrogel preparation.

Preparation of Hydrogel (0.1 mL)

The polymer solution (80 μL) containing the nanocarrier was transferred to a glass vial (12×32 mm, SepCap clear vial, Catalog # C4011-80, National Scientific Company, Rockwood, Tenn.) followed by the crosslinker solution (20 μL). The solution mixture was allowed to stand at room temperature (24° C.). The hydrogel solution started becoming more and more viscous after 8 minutes and ceased to flow from the inverted tube in 11 minutes indicating the formation of hydrogel.

Hydrogel examples with passively entrapped PEG-NHCO-Dye nanocarriers are summarized in Table 4B.

TABLE 4B

| Polymer | Crosslinker | Nanocarrier | Polymer/crosslinker ratio | Time taken for hydrogel formation |
|---|---|---|---|---|
| $PEG_{20\ kDa}$-[SH]$_8$ | HBVS | $PEG_{60\ kDa}$-NHCO-fluorescein | 1:4 | 11 minutes |
| $PEG_{20\ kDa}$-[SH]$_8$* | HBVS | $PEG_{20\ kDa}$-NHCO-methylene blue | 1:4 | 11 minutes |

*Hydrogel was prepared using the procedure described in example 3B.

Example 3C

Preparation of Hydrogel with Passively Entrapped $PEG_{20kDa}$-[CONH-RGDC(SH)-CONH-DOX]$_4$ Nanocarrier Preparation of Sodium Phosphate Buffer (0.1 M, pH 8.00±0.05)

A solution of sodium phosphate dibasic (1 M, Catalog # S-9763, Sigma Aldrich, St. Louis, Mo.) was prepared in a volumetric flask by dissolving 14.2 grams of salt in 100 mL of deionized (DI) water. Similarly, the solution of sodium phosphate monobasic (1M, Catalog # S-0751, Sigma Aldrich, St. Louis, Mo.) was prepared in another flask by dissolving 12.0 grams of salt in 100 mL DI water. 9.32 mL of sodium phosphate dibasic and 0.68 ml of sodium phosphate monobasic solutions were transferred to a beaker. DI water (80.0 mL) was added to the beaker and the pH of the solution was measured as described in example 3A. The pH was adjusted to 8.00 using 0.1 N sodium hydroxide solution (Catalog # SS276-4, Fisher Scientific, Suwanee, Ga.). The buffer was transferred to a volumetric flask and DI water was added to adjust the final buffer volume to 100 mL. Unless otherwise indicated, all reference to DI refers to deionized water. Likewise, unless otherwise indicated, all reference to PB in example 3C refers to 0.1 M phosphate buffer, pH, 8.00.

Preparation of Polymer Solution Containing the Nanocarrier

Four-arm $PEG_{20kDa}$-[NHS]$_4$ (5 mg, 2.5×10$^{-4}$ mM; Catalog # SUNBRIGHT PTE-200GS, NOF America Corporation, White Plains, N.Y.) was weighed in a centrifuge tube and dissolved in PB (50 μL). The $PEG_{20kDa}$-[CONH-RGDC(SH)-CONH-DOX]$_4$ nanocarrier (1.1 mg, 4.6×10$^{-5}$ mM; 100 μg doxorubicin equivalent) was added to this solution and vortexed (<1 minutes) to make a clear solution.

Preparation of Crosslinker Solution

Four-arm $PEG_{20kDa}$-$[SH]_4$ (5 mg, 1 equiv., $2.5\times10^{-4}$ mM; Catalog # SUNBRIGHT PTE-200SH, NOF America Corporation, White Plains, N.Y.) was weighed in a centrifuge tube and dissolved in PB (50 µL) by vortexing for <1 minutes.

Preparation of Hydrogel (0.1 mL)

The polymer solution (50 µL) containing the nanocarrier was transferred to a glass vial (12×32 mm, SepCap clear vial, Catalog # C4011-80, National Scientific Company, Rockwood, Tenn.) followed by the crosslinker solution (50 µL). The solution mixture was allowed to stand at room temperature (24° C.). The hydrogel solution started becoming more and more viscous after 30 minutes and ceased to flow from the inverted tube in 1 hour indicating the formation of hydrogel.

Hydrogel examples with passively entrapped PEG-[CONH-RGDC(SH)-CONH-DOX]$_4$ nanocarriers are summarized in Table 4C.

TABLE 4C

| Polymer | Crosslinker | Nanocarrier | Polymer/ crosslinker ratio | Time taken for hydrogel formation |
|---|---|---|---|---|
| $PEG_{20\,kDa}$-$[NHS]_4$ | $PEG_{20\,kDa}$-$[SH]_4$ | $PEG_{20\,kDa}$-[CONH-RGDC(SH)-CONH-DOX]$_4$ | 1:1 | 60 minutes |
| $PEG_{40\,kDa}$-$[NHS]_4$* | $PEG_{20\,kDa}$-$[SH]_4$ | $PEG_{20\,kDa}$-[CONH-RGDC(SH)-CONH-DOX]$_4$ | 0.5:1 | 60 minutes |
| $PEG_{20\,kDa}$-$[NHS]_4$* | $PEG_{20\,kDa}$-$[SH]_8$ | $PEG_{40\,kDa}$-[CONH-RGDC(SH)-CONH-DOX]$_4$ | 1:1 | 30 minutes |
| $PEG_{40\,kDa}$-$[NHS]_4$* | $PEG_{20\,kDa}$-$[SH]_8$ | $PEG_{40\,kDa}$-[CONH-RGDC(SH)-CONH-DOX]$_4$ | 0.5:1 | 30 minutes |

*Hydrogels prepared using the procedure described in example 3C.

Example 4

Preparation of Nanogel Particles (NPs)

Example 4A

Preparation of Nanogel Particles (NPs) Using Polymer to Cross-Linker Ratio of 1:1

Preparation of Sodium Phosphate Buffer ("PB", 0.1 M, pH=7.4)

A solution of 0.1 M phosphate buffer was prepared by adding 77.4 ml of 1 M $Na_2HPO_4$ and 22.6 ml of 1 M $NaH_2PO_4$ to a beaker. D.I. grade water (800.0 mL) was added and pH was adjusted to 7.4 with 0.1 N sodium hydroxide (NaOH) solution. More DI water was added to make the final volume of 1000 ml. Unless otherwise indicated, all further references to PB refer to 0.1M PB, pH 7.4, prepared in this manner. Likewise, unless otherwise indicated, all references to water refer to D.I. HPLC grade water.

Preparation of Polymer Solution 50 mg (1 equiv.) of hexa-glycerine, octa-polyethylene glycol (ether) ethanethiol (8-Arm PEG-thiol polymer; MW=20,000, SUNBRIGHT® custom synthesized by NOF America, White Plains, N.Y.) was weighed in a 15 ml Greiner centrifuge tube containing a stir bar (1 cm dimension). 3320 µL PB was added to dissolve the PEG-thiol polymer.

Preparation of Crosslinker Solution

Crosslinker 1,6-Hexane-bis-vinylsulfone (HBVS, 2.5 mg, 1 equiv., white solid, MW=266.38, Catalog No. 22334, Pierce Protein Research Products, Thermo Scientific, Rockford, Ill.) was weighed in another 15 mL Greiner centrifuge tube and dissolved in 1680 µL PB.

Preparation of NPs

The crosslinker solution was mixed with the polymer solution and the reaction mixture was stirred (speed 1800 rpm) on a magnetic stirrer (Corning model PC 310, Kent City, Mich.) at room temperature (24° C.) for 1 day. After 1 day, the stirring was stopped and the reaction mixture was filtered sequentially through 5, then 0.65, then 0.22 micron filters (Millipore, Catalogue No. UFC40SV25, UFC40DV25, UFC40GV25, Bellerica, Mass.) that were not pre-rinsed. The filtrate was collected and lyophilized, yielding nanogel particles as a white amorphous solid.

Analysis of NPs

Nanogel particle size was measured using a DynaPro 99, Dynamic Light Scattering (DLS) spectrophotometer (Wyatt Technology Corp., Santa Barbara, Calif.). 1 mg of nanogel particles were taken in 1.5 mL Eppendorf tube and suspended in 1 mL water by gently shaking by hand for about 30 seconds. 20 µL of the nanogel particle dispersion was transferred to a cuvette and placed into the instrument. 20 µL of water was used as blank (reference solvent). Readings were taken utilizing a WyattQELS (Quasi-Elastic-Light-Scattering) using a real time digital correaltor instrument at 25° C. in water (acquisition time was 10 seconds, number acquired=20, laser power=100%). The nanogel mean particle size was found to be 137 nm, with a standard deviation of ±4 nm.

Microscopic Analysis of NPs

Particle morphology and size were confirmed using Transmission Electron Microscope (TEM). 1 mg of nanogel particles were weighed and put in 1.5 mL Eppendorf tube and suspended in 0.2 mL of water by gently shaking by hand for 30 seconds. 25 µl of nanogel particle dispersion drop was placed on a 400-mesh carbon coated copper grid. The solution was wicked off the grid and negatively stained with an aqueous solution of 0.5% uranyl acetate. The grids were scoped on a Philips CM12 (FEI, Hillsboro, Oreg.) transmission electron microscope at 80 kV and images were captured with an AMT digital camera. The nanogel particle size was found to be 20-100 nm confirming the DLS measurement.

TABLE 5A

| Stirring time | Polymer to Cross-linker ratio | NPs size using DLS (FIG. 10) | NPs size using TEM (FIG. 11) |
|---|---|---|---|
| 1 day | 1:1 | 137 nm | 20-100 nm |
| 1 day | 1:0.8* | 122 nm | 20-100 nm |
| 1 day | 1:0.5* | 125 nm | 20-100 nm |

Similar procedure was used for the preparation of nanogel particles using polymer crosslinker ratio 1:0.8 and 1:0.5.

Example 4B

Preparation of Nanogel Particles (NPs) Using Different Stirring Time (1 Day, 2 Days and 3 Days)

The procedure for the preparation of phosphate buffer, preparation of NPs, analysis of NPs and microscopic analysis of NPs were used as it is, as mentioned in example 4A.

Preparation of Polymer Solution 100 mg (1 equiv.) of hexa-glycerine, octa-polyethylene glycol (ether) ethanethiol (8-Arm PEG-thiol polymer; MW=20,000, SUNBRIGHT® custom synthesized by NOF America, White Plains, N.Y.) was weighed in a 15 ml Greiner centrifuge tube containing a stir bar (1 cm dimension). 6640 μL PB was added to dissolve the PEG-thiol polymer.

Preparation of Crosslinker Solution

Crosslinker 1,6-hexane-bis-vinylsulfone (HBVS, 5 mg, 1 equiv., white solid, MW=266.38, Catalog No. 22334, Pierce Protein Research Products, Thermo Scientific, Rockford, Ill.) was weighed in another 15 mL Greiner centrifuge tube and dissolved in 3360 μL PB.

NPs size was found to be 17.6 nm (using DLS) and 20-40 nm (using TEM).

TABLE 5B

| Stirring time | Polymer to cross-linker ratio | NPs size using DLS (FIG. 12) | NPs size using TEM |
|---|---|---|---|
| 1 day | 1:1 | 17.6 nm | 20-40 nm (FIG. 13) |
| 2 day* | 1:1 | 310 nm | 20-300 nm (FIG. 14) |
| 3 day* | 1:1 | 12.5 nm | 20-300 nm (FIG. 14) |

Similar procedure was used for the preparation of NPs using stirring time of 2 days and 3 days.

Example 4C

Preparation of Nanogel Particles Using Surfactant and Different Stirring Time (1 Day, 2 Days and 3 Days)

The procedure for the preparation of phosphate buffer, analysis of NPs and microscopic analysis of NPs were used as it is, as mentioned in example 4A and procedure for the preparation of polymer solution was used as it is, as mentioned in example 4B.

Preparation of Crosslinker Solution

Crosslinker 1,6-hexane-bis-vinylsulfone (HBVS, 5 mg, 1 equiv., white solid, MW=266.38, Catalog No. 22334, Pierce Protein Research Products, Thermo Scientific, Rockford, Ill.) was weighed in another 15 mL Greiner centrifuge tube and dissolved in 3350 μL PB.

Preparation of NPs

The crosslinker solution was mixed with the polymer solution and surfactant polyethylene glycol sorbitan monooleate (0.1% w/v Tween 80, 10 μL, Croda, Edison, N.J.) was added into reaction mixture. The reaction mixture was stirred (speed: 1800 rpm) on a magnetic stirrer (Corning model PC 310, Kent City, Mich.) at room temperature (24° C.) for 1 day. After 1 day, the stirring was stopped and the reaction mixture was filtered sequentially through 5, 0.65, and 0.22 micron filters (Millipore, Catalogue No. UFC40SV25, UFC40DV25, UFC40GV25, Bellerica, Mass.) that were not pre-rinsed. The filtrate was collected and lyophilized, yielding nanogel particles as a white amorphous solid.

NPs size was found to be 10.1 nm (using DLS) and 20-30 nm (using TEM).

TABLE 5C

| Stirring time | Polymer to cross-linker ratio | NPs size using DLS (FIG. 15) | NPs size using TEM |
|---|---|---|---|
| 1 day | 1:1 | 10.1 nm | 20-40 nm (FIG. 13) |
| 2 day* | 1:1 | 3.3 nm | 20-100 nm (FIG. 11) |
| 3 day* | 1:1 | 21.1 nm | 20-100 nm (FIG. 11) |

Similar procedure was used for the preparation of NPs using stirring time of 2 days and 3 days.

Example 4D

Preparation of Nanogel Particles Using Surfactant, Sonication and Different Stirring Time (1 Day)

The procedure for the preparation of phosphate buffer, analysis of NPs and microscopic analysis of NPs were used as it is, as mentioned in example 4A. Procedure for the preparation of polymer solution was used as it is, as mentioned in example 4B, and procedure for the preparation of polymer cross-linker solution was used as it is, as mentioned in 4C.

Preparation of NPs

The crosslinker solution was mixed with the polymer solution and surfactant polyethylene glycol sorbitan monooleate (0.1% w/v Tween 80, 10 μL, Croda, Edison, N.J.) was added into reaction mixture. The reaction mixture was sonicated for 10 min using probe sonicator [Microson™ XL2000, Ultra Sonic Liquid Processor, Farmingdale, N.Y., setting 4 watts (RMS)]. The reaction mixture was stirred (speed: 1800 rpm) on a magnetic stirrer (Corning model PC 310, Kent City, Mich.) at room temperature (24° C.) for 1 day. After 1 day, the stirring was stopped and the reaction mixture was filtered sequentially through 5, 0.65, and 0.22 micron filters (Millipore, Catalogue No. UFC40SV25, UFC40DV25, UFC40GV25, Bellerica, Mass.) that were not pre-rinsed. The filtrate was collected and lyophilized, yielding nanogel particles as a white amorphous solid.

NPs size was found to be 4.3 nm (using DLS) and 20-40 nm (using TEM).

TABLE 5D

| Stirring time | Polymer to cross-linker ratio | NPs size using DLS (FIG. 16) | NPs size using TEM |
|---|---|---|---|
| 1 day | 1:1 | 4.3 nm | 20-40 nm (FIG. 13) |
| 2 day* | 1:1 | 4.3 nm | 20-40 nm (FIG. 13) |
| 3 day* | 1:1 | 37.1 nm | 20-100 nm (FIG. 11) |

Similar procedure was used for the preparation of NPs using surfactant, sonication with stirring time of 2 days and 3 days.

5. Examples of Aggregated Nanogel Particles (ANPs)

Example 5A

Preparation of Aggregated Nanogel Particles (ANPs) Using Surfactant, Sonication and Different Stirring Time The procedure for the preparation of phosphate buffer was used as it is, as mentioned in example 4A. Procedure for the preparation of polymer solution was used as it is, as mentioned in example 4B, and procedure for the preparation of cross-linker solution was used as it is, as mentioned in example 4C.

Preparation of ANPs

The crosslinker solution was mixed with the polymer solution and surfactant polyethylene glycol sorbitan monooleate (0.1% w/v Tween 80, Croda, Edison, N.J.) was added into the reaction mixture. The reaction mixture was sonicated for 10 min using probe sonicator [Microson™ XL2000, Ultra Sonic Liquid Processor, Farmingdale, N.Y., setting 4 watts (RMS)]. The reaction mixture was stirred (speed 1800 rpm) on a magnetic stirrer (Corning model PC 310, Kent City, Mich.) at room temperature (24° C.) for 1 day. After 1 day, the stirring was stopped and the filtrate was collected and lyophilized, yielding nanogel particles as a white amorphous solid.

Analysis of ANPs

ANPs size was measured using a DynaPro 99, Dynamic Light Scattering (DLS) spectrophotometer (Wyatt Technology Corp., Santa Barbara, Calif.). 1 mg of ANPs were taken in 1.5 mL Eppendorf tube and suspended in 1 mL of water by gently shaking by hand for about 30 seconds. 20 μL of the ANPs dispersion was transferred to a cuvette and placed into the instrument. 20 μL of water was used as blank (reference solvent). Readings were taken utilizing a WyattQELS (Quasi-Elastic-Light-Scattering) using a real time digital correaltor instrument at 25° C. in water (acquisition time: 10 seconds, number acquired: 20, laser power: 100%). The ANPs size was found to be 26-138 nm.

Microscopic Analysis of ANPs

Particle morphology and size were confirmed using Transmission Electron Microscope (TEM). 1 mg of ANPs were weighed and put in 1.5 mL Eppendorf tube and suspended in 0.2 mL of water by gently shaking by hand for 30 seconds. 25 μl of ANPs dispersion drop was placed on a 400-mesh carbon coated copper grid. The solution was wicked off the grid and was negatively stained with an aqueous solution of 0.5% uranyl acetate. The grids were scoped on a Philips CM12 (FEI, Hillsboro, Oreg.) transmission electron microscope at 80 kV and images were captured with an AMT digital camera. The ANPs size was found to be 20-100 nm.

TABLE 6A

| Stirring time | Polymer to Cross-linker ratio | ANPs size using DLS (FIG. 17) | ANPs size using TEM |
|---|---|---|---|
| 1 day | 1:1 | 26, 138 | 20-100 nm (FIG. 11) |
| 2 days* | 1:1 | 26, 132 | 20-100 nm (FIG. 11) |
| 3 days* | 1:1 | 23, 73 | 20-300 nm (FIG. 14) |
| 4 days* | 1:1 | 20, 103 | ~10 micron (FIG. 18) |
| 5 days* | 1:1 | 17, 95, 286 | ~18 micron (FIG. 19) |
| 6 days* | 1:1 | 43, 153, 3576 | ~24 micron (FIG. 20) |
| 7 days* | 1:1 | 30, 126, 3578 | ~30 micron (FIG. 21) |

Similar procedure was used for the preparation of ANPs using surfactant and sonication with different stirring time of 2 days, 3 days, 4 days, 5 days, 6 days and 7 days.

Example 5B

Preparation of Stabilized ANPs Using 8-Arm PEG-thiol Polymer

The procedure for the preparation of phosphate buffer was used as it is, as mentioned in example 4A. The procedure for the preparation of polymer solution was used as it is, as mentioned in example 4B. The procedure for the preparation of polymer cross-linker solution was used as it is, as mentioned in example 4C.

Preparation of Stabilized ANPs

The crosslinker solution was mixed with the polymer solution and surfactant polyethylene glycol sorbitan monooleate (0.1% w/v Tween 80, 10 μL, Croda, Edison, N.J.) was added into reaction mixture. The reaction mixture was sonicated for 10 min using probe sonicator [Microson™ XL2000, Ultra Sonic Liquid Processor, Farmingdale, N.Y., setting 4 watts (RMS)]. The reaction mixture was stirred (speed: 1800 rpm) on a magnetic stirrer (Corning model PC 310, Kent City, Mich.) at room temperature (24° C.) for 25 days. 300 mg of hexa-glycerine, octa-polyethylene glycol (ether) ethanethiol (8-Arm PEG-thiol polymer, white solid, MW=20,000, obtained from NOF America) was weighed in a 15 ml Greiner centrifuge tube, 3 ml solution of reaction mixture (after 25 days stirring) was transferred into 15 mL Greiner centrifuge tube containing 300 mg of 8-Arm PEG-thiol polymer. The solution was agitated slowly using spatula (Cat. No. 21-40125-B, Fisher brand Micro spatula, hayman 6$^{1/4}$") for 5 minutes. The agitated sample was lyophilized for 2-days (FreeZone 2.5, Labconco Corporation), yielding stable ANPs as a white solid (Scheme 3).

Analysis of Stabilize ANPs Using Coulter Counter

ANPs particle size was measured using a Multisizer™ 3 Coulter Counter. (560 μm aperture tube Beckman Coulter Corporation, Miami, Fla.). 1 mg of ANPs were taken in 1 ml Eppendorf tube and dissolved in 1 ml of water (HPLC grade). 100 μl of ANPs dispersion were mixed and transferred to a Coulter Counter cuvette and cuvette was placed into the instrument. 10 mL Isoton was used a blank (reference solvent, Catalog #8546719, Beckman Coulter, Inc., Fullerton, Calif.).

The ANPs size was found to be 60-70 micron using coulter counter (FIG. 22).

Example 5C

Preparation of Stabilized DYE-ANPs

The procedure for the preparation of phosphate buffer was used as it is, as mentioned in example 4A. The procedure for the preparation of polymer solution was used as it is, as mentioned in example 4B. The procedure for the preparation of polymer cross-linker solution was used as it is, as mentioned in example 4C. The procedure for the microscopic analysis of ANPs was used as it is, as mentioned in example 5C.

Preparation of Stabilized DYE-ANPs

The crosslinker solution was mixed with the polymer solution and surfactant polyethylene glycol sorbitan monooleate (0.1% w/v Tween 80, 10 μL, Croda, Edison, N.J.) was added into the reaction mixture. The reaction mixture was sonicated for 10 min using probe sonicator [Microson™ XL2000, Ultra Sonic Liquid Processor, Farmingdale, N.Y., setting 4 watts (RMS)]. The reaction mixture was stirred (speed: 1800 rpm) on a magnetic stirrer (Corning model PC 310, Kent City, Mich.) at room temperature (24° C.) for 25 days. 300 mg of DYE-carrier (blue powder, MW=~21,000, self prepared) was weighed in a 15 ml Greiner centrifuge tube, 3.5 ml solution of ANPs reaction mixture (after 25 days stirring) was transferred into 15 mL Greiner centrifuge tube containing 300 mg of dye-polymer. The solution was agitated slowly using spatula (Catalog #21-40125-B, Fisher brand Micro spatula, Hayman 6$^{1/4}$") for 5 minutes. The agitated sample was lyophilized for 2-days (FreeZone 2.5, Labconco Corporation), yielding stable DYE-ANPs as a blue solid. The DYE-ANPs size was found to be 70 micron using coulter counter (FIG. 22).

Example 5D

Preparation of Stabilized DRUG-ANPs

The procedure for the preparation of phosphate buffer was used as it is, as mentioned in example 4A. The procedure for the preparation of, polymer solution was used as it is, as mentioned in example 4B. The procedure for the preparation of polymer cross-linker solution was used as it is, as mentioned in example 4C. The procedure for the microscopic analysis of ANPs was used as it is, as mentioned in example 5A.
Preparation of Stabilize DRUG-ANPs The crosslinker solution was mixed with the polymer solution and surfactant polyethylene glycol sorbitan monooleate (0.1% w/v Tween 80, 10 µL, Croda, Edison, N.J.) was added into reaction mixture. The reaction mixture was sonicated for 10 min. using probe sonicator [Microson™ XL2000, Ultra Sonic Liquid Processor, Farmingdale, N.Y., setting 11 watts (RMS)]. The reaction mixture was stirred (speed: 1800 rpm) on a magnetic stirrer (Corning model PC 310, Kent City, Mich.) at room temperature (24° C.) for 25 days. 300 mg of DRUG-polymer (blue powder, MW=542, self prepared) was weighed in a 15 ml Greiner centrifuge tube, 3.5 ml solution of ANPs reaction mixture (after 25 days stirring) was transferred into 15 mL Greiner centrifuge tube containing 300 mg of drug-carrier. The solution was agitated slowly using spatula (Catalog #21-40125-B, Fisher brand Micro spatula, Hayman 6$^{1/4"}$) for 5 minutes. The agitated sample was lyophilized for 2-days (FreeZone 2.5, Labconco Corporation), yielding stable DRUG-ANPs as a white solid.

The ANPs size was found to be 60-70 micron using coulter counter (FIG. 22).

Example 5E

Preparation of Reduced Size DYE-ANPs by Sonicating the Particles

Sonication of DYE-ANPs

To reduce the particle size of the DYE-ANPs (80-100 micron), DYE-ANPs (3 mg) were mixed in (500 µL) phosphate buffered saline (USP Grade). The sample was sonicated for 1 min at 4 watts (RMS) using probe sonicator (Microson Ultra Cell Sonic Disruptor).
Analysis of Particle Size Using Coulter Counter ANPs particle size was measured using a Multisizer™ 3 Coulter Counter (560 µm aperture tube Beckman Coulter Corporation, Miami, Fla.). 1 mg of DYE-ANPs were taken in 1 ml Eppendorf tube and dissolved in 1 ml of water (HPLC grade). 100 µl of ANPs dispersion were mix with was transferred to a Coulter Counter cuvette and placed into the instrument. 10 mL Isoton (Catalog #8546719, Beckman Coulter, Inc., Fullerton, Calif.) was used a blank (reference solvent). The sonication time 1.5 min reduced the particle size from 80-100 micron to 50-60 micron.

TABLE 6E

| Sr. No. | Instrument setting | Particle size | Sonication time |
|---|---|---|---|
| 1 | 4 watts (RMS) | 50-60 micron (FIG. 23) | 1.0 min |

TABLE 6E-continued

| Sr. No. | Instrument setting | Particle size | Sonication time |
|---|---|---|---|
| 2* | 4 watts (RMS) | 30-50 micron (FIG. 24) | 1.5 min |
| 3* | 4 watts (RMS) | 10-30 micron (FIG. 25) | 2.0 min |

*Similar procedure was used for the preparation of 30-50 micron and 10-30 micron DYE-ANPs.

Example 5F

Preparation of Reduced Size DRUG-ANPs (10-30 Micron) by Sonicating the Particles The procedure for the sonication of DYE-ANPs and analysis of particle size using Coulter Counter were used as it is, as mentioned in example 5E. The sonication time 2 min showed that particle size reduces from 60-70 micron to 10-30 micron (FIG. 25).

Example 5G

Preparation of DYE-Carrier

HiLyte Fluor™ 750C2 maleimide (3 mg, Near IR dye, Abs/Em=754/778 nm, MW=1222.5, Catalog No. 81269, AnaSpec Corporation, San Jose, Calif.) was weighed in 50 ml round bottom flask containing a stir bar (1 cm dimension) and dissolved in 10 ml of N,N-dimethyl formamide (DMF). 200 mg of hexa-glycerine, octa-polyethylene glycol (ether) ethanethiol (8-Arm PEG-thiol polymer; white solid, MW=20,000, obtained from NOF America) was mixed with the HiLyte Fluor™ 750 C2 maleimide solution. N,N-Diisopropylethylamine (DIEA, 0.0132686 ml, molecular weight 129.7) was added into the reaction mixture and the reaction mixture was stirred (speed: 1800 rpm) on a magnetic stirrer (Corning model PC 310, Kent City, Mich.) at room temperature (24° C.) for half hour. After half hour, reaction mixture was poured drop wise into pre-cooled diethyl ether (40 ml, Catalog #9237-33, JT Baker, Phillipsburg, N.J.) to precipitate the crude product. The ether solution containing the precipitate was centrifuged for 45 min. The supernatant ether was removed; the process was repeated 2 times using 25 ml ether each time. Finally the ether was removed and the flask containing the product was dried under argon gas. Yield obtained was 70%.

Example 5H

Preparation of DRUG-Carrier

Step 1

The mercaptoethanol (1 equiv., Sigma, Catalog No. M6250, St. Louis, Mo.) was weighed in 50 ml round bottom flask containing a stir bar (1 cm dimension) and dissolved in methanol (7.5 ml). Aldrithiol-2 (1.2 equiv., Aldrich, Catalog No. 143049, St. Louis, Mo.) was added to this solution and the reaction mixture was stirred (speed: 1800 rpm) on a magnetic stirrer (Corning model PC 310, Kent City, Mich.) at room temperature (24° C.) for 24 h. Yield obtained was 60% (TP-mercaptoethanol), crude reaction mixture were used for the next step.
Step 2

For the preparation of drug carrier, TP-mercaptoethanol (1 equiv.) was weighed in 50 ml round bottom flask containing a stir bar (1 cm dimension) and dissolved in dichloromethane (10 ml, Catalog # C326850010, Acros Organics, NJ). Indomethacin (1.2 equiv., Fluka, Molecular weight 357.81, Catalog No. 57413, Buchs, Italy) and N,N-Diisopropylethylamine (1.2 equiv., Sigma Aldrich, Catalog #387649, St. Louis, Mo.) was added to this solution and the reaction mixture was stirred (speed: 1800 rpm) on a magnetic stirrer (Corning model PC 310, Kent City, Mich.) at room temperature (24° C.) for 6 hours. Yield obtained was 73%.

Example 5I

Biodistribution Studies of DYE-ANPs (50-60 Micron)

Biodistribution studies with aggregated nanogel particles (ANPs, 50-60 micron) containing covalently labeled HiLyte750 dye (DYE-ANPs) were performed daily for 1 week period to better understand their pharmacokinetics/residence time behavior in lung. DYE-ANPs (4 mg in 600 μL of 0.9% sodium chloride INJ., USP, Hospira, INC, Lake Forest, Ill.) were administered to male Sprague-Dawley rats (Hilltop Animal Labs., Scottdale, Pa.) through tail vein injection. Biodistribution of ANPs was determined using a Xenogen IVIS 100 Imaging System (Xenogen Corporation, California, Calif. now part of Caliper Life Sciences, Hopkinton, Mass.). Instrument settings were as follows: Mode: Fluorescence; Exposure time: 60 seconds; Binning medium: F/stop-1; Excitation filter: ICG; Emission filter: ICG; Photographic: 0.2; Subject height: 1.5 cm; Field of view: C/25 cm. DYE-ANPs were found to accumulate in the lung within 30 minutes post administration and the majority of the DYE-ANPs remained in the lung for more than 7 days post administration (FIG. 26).

TABLE 6I

| Dose | Injected particle size | Animal used for studies | DYE-ANPs accumulation/ residence time in lung |
|---|---|---|---|
| 4 mg* in 600 μL | 50-60 | Rat | Accumulated in the lung: 30 minutes<br>Remained in the lung: 7 days (FIG. 26) |
| 0.25 mg[1] in 600 μL | 30-50 | Rat | Accumulated in the lung: 3 h<br>Remained in the lung: 18 h (FIG. 27) |
| 0.5 mg[1] in 600 μL | 30-50 | Rat | Accumulated in the lung: 3 h<br>Remained in the lung: 18 h (FIG. 27) |
| 1 mg[1] in 600 μL | 30-50 | Rat | Accumulated in the lung: 3 h<br>Remained in the lung: 18 h (FIG. 27) |
| 2 mg[1] in 600 μL | 30-50 | Rat | Accumulated in the lung: 3 h<br>Remained in the lung: 18 h (FIG. 27) |
| 4 mg[2] in 600 μL | 10-30 | Rat | Accumulated in the lung: 18 h<br>Remained in the lung: 6 days (FIG. 28) |
| 2 mg[3] in 600 μL | 10-30 | Mice | Remained in the lung: 18 h (FIG. 29) |

*Similar procedure was used for the biodistribution studies with DYE-ANPs of size 30-40 micron and 10-30 micron in rats and mice[1, 2 & 3].
[1]Injection samples were collected at 3, 6, and 18 h for IVIS.
[2]Injection samples were collected at 18 h, 2 days, 4 days, and 6 days for IVIS.
[3]Injection samples were collected at 18 h for IVIS.

Example 5J

In Vivo Studies of DRUG-ANPs (10-30 Micron)

In vivo studies of aggregated nanogel particles (ANPs, 10-30 micron) containing covalently attached indomethacin (DRUG-ANPs) were performed to better understand the pharmacokinetics/residence time behavior of the DRUG-ANPs in lung. DRUG-ANPs (4 mg in 600 μL, 0.9% sodium chloride INJ., USP, Hospira, INC, Lake Forest, Ill.) were administered to male Sprague-Dawley rats (Hilltop Animal Labs, Scottsdale, Pa.) through tail vein injection. Lung samples were collected at 18 h, 2, 4, 5, and 6 days post administration, embedded in paraffin and sections stained with H & E (Magnification 100×). No inflammation was found in histology studies (FIG. 30).

Example 6A

Preparation of $PEG_{20kDa}$-[S-fluorescein]$_3$[SH]$_5$ Nanocarrier to Obtain Crosslinked Nanocarrier Hydrogel Preparation of Sodium Phosphate Buffer (0.1 M, pH=7.40±0.05) Containing Ethylene Diamine Tetraacetate (EDTA, 5 mM)

Sodium phosphate dibasic (1 M, Catalog # S-9763, Sigma Aldrich, St. Louis, Mo.) and sodium diphosphate monobasic solutions (1M, Catalog # S-0751, Sigma Aldrich, St. Louis, Mo.) were prepared as described in example 3C. 7.74 mL of sodium phosphate dibasic and 2.26 ml sodium phosphate monobasic solutions were transferred to a beaker. DI water (80.0 mL) was added to the beaker and EDTA was dissolved (186.1 mg, Sigma Aldrich, St Louis, Mo.) in it. The pH was measured as described in example 3A; the pH was adjusted to 7.40 using 0.1 N sodium hydroxide solution (Catalog # SS276-4, Fisher Scientific, Suwanee, Ga.). The buffer was transferred to a volumetric flask and DI water was added to adjust the final buffer volume to 100 mL. Unless otherwise indicated, all reference to DI refers to deionized water. Likewise, unless otherwise indicated, all reference to PB in example 6A refers to this buffer.

Preparation of Nanocarrier

The thiol-functionalized eight-arm poly(ethylene glycol) polymer ($PEG_{20kDa}$-[SH]$_8$, 100 mg, 4.65×10$^{-3}$ mM; Catalog # SUNBRIGHT HGEO-200SH, NOF America Corporation, White Plains, N.Y.) was weighed in a 50 mL centrifuge tube and PB (10.0 mL) was added. The mixture was gently stirred (1000 rpm) at room temperature (24° C.) to obtain a clear solution. Fluorescein-5-maleimide (3 equiv., 5.97 mg; Catalog #81405, Anaspec, San Jose, Calif.) was dissolved in N, N-dimethyl formamide (0.5 mL, Catalog # EM-DX1727-6, VWR International, Pittsburgh, Pa.) and added to the polymer solution. The centrifuge tube containing the reaction mixture was covered with aluminum foil (to maintain dark conditions) and stirred (1000-1500 rpm) at room temperature (24° C.) for overnight period (~12 hours). After 12 hours, the stirring was stopped.

Purification of Nanocarrier

Nanocarrier was purified by GPC on Sephadex G50 column in dark, using DI water as eluent as described in example 3A. Reaction mixture (10×1.0 mL) was loaded onto the column and eluted using DI water; the high molecular weight nanocarrier eluted first followed by the low molecular weight fluorescein. High molecular weight fractions were pooled together and lyophilized for 5-days (Labconco, FreeZone 2.5 plus, temperature: −84° C.; pressure: 0.010 millibar). Nanocarrier was obtained as yellow flakes (76.3 mg).

Characterization of Nanocarrier

The nanocarrier was characterized on Waters Breeze GPC system (Waters Corporation, Milford, Mass.) as described in example 3A. The unmodified polymer showed retention time of 8.9 minutes whereas the nanocarrier showed the retention time of 8.0 minutes. The unmodified polymer showed a peak in refractive index panel but not the UV panel because PEG does not absorb at 480 nm, however, nanocarrier showed peak in UV panel too due to the presence of fluorescein, which strongly absorbs at 480 nm wavelengths.

Different nanocarrier examples are summarized in Table 6A.

TABLE 7A

| Nanocarrier | Polymer | Dye | Yield (mg) |
|---|---|---|---|
| $PEG_{20kDa}$-[S-fluorescein]$_3$[SH]$_5$ | $PEG_{20\ kDa}$-[SH]$_8$ | Fluorescein-5-maleimide (3 equiv.) | 76.3 |
| $PEG_{20\ kDa}$-[S-fluorescein]$_1$[SH]$_7$* | $PEG_{20\ kDa}$-[SH]$_8$ | Fluorescein-5-maleimide (1 equiv.) | 84.2 |
| $PEG_{20\ kDa}$-[S-fluorescein]$_{0.5}$[SH]$_{7.5}$* | $PEG_{20\ kDa}$-[SH]$_8$ | Fluorescein-5-maleimide (0.5 equiv.) | 84.0 |
| $PEG_{20\ kDa}$-[S-methylene blue]$_3$[SH]$_5$* | $PEG_{20\ kDa}$-[SH]$_8$ | Methylene blue maleimide (3 equiv.) | |
| $PEG_{20\ kDa}$-[S-methylene blue]$_1$[SH]$_7$* | $PEG_{20\ kDa}$-[SH]$_8$ | Methylene blue maleimide (1 equiv.) | 69.1 mg |
| $PEG_{20\ kDa}$-[S-methylene blue]$_{0.5}$[SH]$_{7.5}$* | $PEG_{20\ kDa}$-[SH]$_8$ | Methylene blue maleimide (0.5 equiv.) | |

*Nanocarriers prepared using the procedure described in example 6A. Methylene blue maleimide was obtained from ATTO-TEC GmbH, Siegen, Germany (Catalog # AD MB-2-45).

Example 6B

Preparation of Hydrogel from Crosslinked $PEG_{20kDa}$-[CONH-RGDC(SH)-CONH-DOX]$_4$ Nanocarrier Preparation of Sodium Phosphate Buffer Sodium phosphate buffer (0.1 M; pH, 8.00±0.05) was prepared as described in example 3C. Unless otherwise indicated, all reference to PB in example 6B refers to this buffer.

Preparation of Nanocarrier Solution

Four-arm $PEG_{20kDa}$-[CONH-RGDC(SH)-CONH-DOX]$_4$ nanocarrier (1.1 mg, 4.6×10$^{-5}$ mM; 100 μg doxorubicin equivalent) was weighed in a centrifuge tube and dissolved in PB (50 μL) by vortexing for <1 minutes.

Preparation of Crosslinker Solution

Crosslinker solution was prepared in a centrifuge tube by dissolving $PEG_{20kDa}$-[S-TP]$_4$ (5 mg, 2.5×10$^{-4}$ mM) in PB (50 μL) by vortexing for <1 minutes.

Preparation of Hydrogel (0.1 mL)

The nanocarrier solution (50 μL) was transferred to a glass vial (12×32 mm, SepCap clear vial, Catalog # C4011-80, National Scientific Company, Rockwood, Tenn.) followed by the crosslinker solution (50 μL). The solution mixture was allowed to stand at room temperature (24° C.). The solution became viscous but did not set into hydrogel because nanocarrier concentration was lower than the preferred composition.

Hydrogel examples with nanocarrier concentration below the preferred composition are summarized in Table 6B.

TABLE 7B

| Nanocarrier | Crosslinker | Nanocarrier/Crosslinker ratio | Time taken for hydrogel formation |
|---|---|---|---|
| $PEG_{20\ kDa}$-[CONH-RGDC(SH)-CONH-DOX]$_4$ | $PEG_{20\ kDa}$-[S-TP]$_4$ | 1:5.4 | No hydrogel |
| $PEG_{20\ kDa}$-[CONH-RGDC(SH)-CONH-DOX]$_4$* | $PEG_{20\ kDa}$-[S-TP]$_8$ | 1:5.4 | No hydrogel |
| $PEG_{20\ kDa}$-[CONH-RGDC(SH)-CONH-DOX]$_4$* | $PEG_{20\ kDa}$-[NHS]$_4$ | 1:5.4 | No hydrogel |
| $PEG_{20\ kDa}$-[CONH-RGDC(SH)-CONH-DOX]$_4$* | $PEG_{40\ kDa}$-[NHS]$_4$ | 1:2.7 | No hydrogel |
| $PEG_{40\ kDa}$-[CONH-RGDC(SH)-CONH-DOX]$_4$* | $PEG_{20\ kDa}$-[S-TP]$_4$ | 1:4.5 | No hydrogel |
| $PEG_{40\ kDa}$-[CONH-RGDC(SH)-CONH-DOX]$_4$* | $PEG_{20\ kDa}$-[S-TP]$_8$ | 1:4.5 | No hydrogel |
| $PEG_{40\ kDa}$-[CONH-RGDC(SH)-CONH-DOX]$_4$* | $PEG_{20\ kDa}$-[NHS]$_4$ | 1:4.5 | No hydrogel |

*Hydrogels prepared using the procedure described in example 6B.

Example 6C

Preparation of Hydrogel from Crosslinked $PEG_{20kDa}$-[CONH-RGDC(SH)-CONH-DOX]$_4$[SH]$_4$ Nanocarrier Preparation of Sodium Phosphate Buffer Sodium phosphate buffers with pH 8.00±0.05 (0.1 M) and 7.44 (0.02 M) were prepared as described in example 3B and 3C.

Preparation of Nanocarrier Solution

Eight-arm $PEG_{20kDa}$-[CONH-RGDC(SH)-CONH-DOX][SH]$_4$ nanocarrier (5 mg, 2.5×10$^{-4}$ mM) is weighed in a centrifuge tube and dissolve in buffer solution (50 μL, 0.02 M, pH=7.44) by vortexing for <1 minutes.

Preparation of Crosslinker Solution

The crosslinker, $PEG_{3.4kDa}$-[S-TP]$_2$ (3.4 mg, 1.0×10$^{-3}$ mM, 4.0 equiv.) is weighed in a centrifuge tube and dissolve in buffer (50 μL, 0.02 M, pH=7.44) by vortexing for <1 minutes.

Preparation of Hydrogel (0.1 mL)

The nanocarrier solution (50 μL) is transferred to a glass vial (12×32 mm, SepCap clear vial, Catalog # C4011-80, National Scientific Company, Rockwood, Tenn.) followed by the crosslinker solution (50 μL). The solution mixture is allowed to stand at room temperature (24° C.). The solution ceases to flow from inverted tube indicating the formation of hydrogel in 10 minutes.

Hydrogel examples with crosslinked nanocarriers are summarized in Table 6C.

TABLE 7C

| Nanocarrier | Crosslinker | Nanocarrier/Crosslinker ratio | Buffer | Time taken for hydrogel formation |
|---|---|---|---|---|
| $PEG_{20\ kDa}$-[CONH-RGDC(SH)-CONH-DOX]$_4$[SH]$_4$ | $PEG_{3.4\ kDa}$-[S-TP]$_2$ | 1:4 | 0.02M; pH, 7.44 | |
| $PEG_{20\ kDa}$-[CONH-RGDC(SH)-CONH-DOX]$_4$[SH]$_4$* | $PEG_{10\ kDa}$-[S-TP]$_4$ | 1:2 | 0.02M; pH, 7.44 | |
| $PEG_{20\ kDa}$-[CONH-RGDC(SH)-CONH-DOX]$_4$[SH]$_4$* | $PEG_{20\ kDa}$-[S-TP]$_8$ | 1:1 | 0.02M; pH, 7.44 | |
| $PEG_{20\ kDa}$-[CONH-RGDC(SH)-CONH-DOX]$_4$[SH]$_4$* | $PEG_{3.4\ kDa}$-[NHS]$_2$ | 1:4 | 0.1M, pH = 8.00 | |
| $PEG_{20\ kDa}$-[CONH-RGDC(SH)-CONH- | $PEG_{20\ kDa}$-[NHS]$_4$ | 1:2 | 0.1M, pH = 8.00 | |

TABLE 7C-continued

| Nanocarrier | Crosslinker | Nanocarrier/ Crosslinker ratio | Buffer | Time taken for hydrogel formation |
|---|---|---|---|---|
| DOX]$_4$[SH]$_4$* | | | | |
| PEG$_{20\,kDa}$-[S-fluorescein]$_1$[SH]$_7$* | PEG$_{3.4\,kDa}$-[S-TP]$_2$ | 1:4 | 0.02M, pH = 7.44 | |
| PEG$_{20\,kDa}$-[S-fluorescein]$_1$[SH]$_7$ | PEG$_{20\,kDa}$-[S-TP]$_4$ | 1:2 | 0.02M, pH = 7.44 | |
| PEG$_{20\,kDa}$-[S-fluorescein]$_1$[SH]$_7$* | PEG$_{3.4\,kDa}$-[NHS]$_2$ | 1:4 | 0.1M, pH = 8.00 | |
| PEG$_{20\,kDa}$-[S-fluorescein]$_1$[SH]$_7$* | PEG$_{20\,kDa}$-[NHS]$_4$ | 1:2 | 0.1M, pH = 8.00 | |
| PEG$_{20\,kDa}$-[S-methylene blue]$_1$[SH]$_7$* | PEG$_{3.4\,kDa}$-[S-TP]$_2$ | 1:4 | 0.02M, pH = 7.44 | |
| PEG$_{20\,kDa}$-[S-methylene blue]$_1$[SH]$_7$* | PEG$_{3.4\,kDa}$-[NHS]$_2$ | 1:2 | 0.1M, pH = 8.00 | |

*Hydrogels prepared using procedure described in example 6B.

Example 7A

Non-Invasive Detection of PEG$_{12kDa}$-NHCO-fluorescein Nanocarrier in Rats Breast Ducts Animal Six-weeks old, female Sprague-Dawley rats were obtained (Hilltop Lab Animals, Inc., Scottdale, Pa.) and housed in Rutgers Laboratory Animal Services facility accredited by Association for the Assessment and Accreditation of Laboratory and Care International (AAALAC). They were maintained on a 12-hour light/dark cycle and received laboratory chow and water ad libitum. Animals were housed three per cage and allowed to acclimatize at least 1-day prior to the studies. All experiments were carried out under established federal regulations and animal protocols (protocol #05-026) approved by the Rutgers University Institutional Animal Care and Use Committee. A day prior to the study, the rat body was clipped with a clipper under anesthesia with isoflurane (AErrane, Catalog # NDC 10019-773-40, Baxter, Deerfield, Ill.) and Veet (Reckitt Benckiser North America, Inc., Parsippany, N.J.) was applied on the clipped skin. Veet was removed 5 minutes post application and rats were washed with warm water and wiped with dry paper towels.

Preparation of Nanocarrier Solution for Injection

Nanocarrier was weighed (5.2 mg) in a 2 ml eppendorf tube and 0.87 ml of injectable 0.9% sodium chloride solution (USP grade, Hospira Inc, Lake Forest, Ill.) was added using 1 ml tuberculin syringe (Catalog #309602, BD, Franklin Lakes, N.J.). The tube was tapped to dissolve the nanocarrier and the final concentration of the nanocarrier solution was 0.5 mM.

Intraductal Nanocarrier Injection in Rats

Rat under anesthesia with isoflurane (AErrane, Catalog # NDC 10019-773-40, Baxter, Deerfield, Ill.) was placed under a surgical microscope (Stereomaster, Fisher Scientific, Suwanee, Ga.) equipped with a ring lamp, and magnification was adjusted to operator's comfort to aid the injection procedure. Nanocarrier solution (0.1 ml) was injected into the third teat (counting from the head) using a 33 G needle (Catalog #7747-01, Hamilton, Reno, Nev.) attached to a 0.1 ml Hamilton syringe (Catalog #81020, Hamilton, Reno, Nev.). The process was repeated with two more rats.

Non-Invasive Nanocarrier Detection in Rats

After the nanocarrier administration, rats were immediately imaged (one at a time) on IVIS 100 optical imaging system (Xenogen Imaging Technologies, now part of Caliper Life Sciences, Hopkinton, Mass.). The system was set up as follows: Level: High; Em/Ex: GFP; Bin: HR (4); FOV 25; Aperture: f4; and Shutter: 1 s. The animals were then imaged at 1, 2, 3, 4, 5, 6, 7, 8, 9, 10, 11, 12, 24 and 32 hours (till the nanocarrier is cleared) post administration. Fluorescent intensity of the injected area subtracted with that of uninjected distal area was used for nanocarrier quantitation in ducts.

Non-invasive detection studies of different nanocarriers in rats breast duct are summarized in table 7A.

TABLE 8A

| Nanocarrier | Dose (nmol/teat) | Number of rats | Retention in ducts |
|---|---|---|---|
| PEG$_{12\,kDa}$-NHCO-fluorescein | 50 | 3 | 8 |
| PEG$_{20\,kDa}$-NHCO-fluorescein* | 50 | 3 | 15 |
| PEG$_{30\,kDa}$-NHCO-fluorescein* | 50 | 3 | 19 |
| PEG$_{20\,kDa}$-[NHCO-fluorescein]$_4$* | 50 | 3 | 12 |
| PEG$_{20\,kDa}$-[NHCO-fluorescein]$_8$* | 50 | 3 | 14 |
| PEG$_{40\,kDa}$-NHCO-fluorescein* | 50 | 3 | 28 |
| PEG$_{40\,kDa}$-[NHCO-fluorescein]$_4$* | 50 | 3 | 24 |
| PEG$_{60\,kDa}$-NHCO-fluorescein* | 50 | 3 | 32 |
| PEG$_{20\,kDa}$-LG-DOX* | 259 Dox equivalents | 1 | 3.5 |
| PEG$_{20\,kDa}$-[CONH-RGDC(SH)-CONH-Dox]$_4$* | 172 Dox equivalents | 3 | 5.5 |
| PEG$_{40\,kDa}$-[CONH-RGDC(SH)-CONH-Dox]$_4$* | 172 Dox equivalents | 3 | 5.5 |

*All non-invasive detection studies were done as described in example 7A. Longer time durations (~7-days) were used for high molecular weight nanocarriers.

Example 7B

Non-Invasive Detection of Hydrogel with Passively Entrapped PEG$_{20kDa}$-[CONH-RGDC(SH)-CONH-DOX]$_4$ Nanocarrier in Rats Breast Duct Animal Six-weeks old female Sprague-Dawley rats were obtained and treated as described in example 7A. All experiments were carried out under established federal regulations and animal protocols (protocol #05-026) approved by the Rutgers University Institutional Animal Care and Use Committee.

Preparation of Buffer

Sodium phosphate buffer (PB, 0.1 M, pH=8.00) was prepared as described in example 3C. Unless otherwise mentioned, all reference to PB in example 7B refers to this buffer.

Preparation of Hydrogel Solution

Nanocarrier, PEG$_{20kDa}$-[CONH-RGDC(SH)-CONH-DOX]$_4$ was weighed (6.6 mg, $3.3 \times 10^{-4}$ mM, 600 µg Dox equivalents) in a 2 ml eppendorf tube and dissolved in PB (0.6 mL, 0.1 M, pH=8.00). PEG$_{20kDa}$-[NHS]$_4$ polymer (45 mg, $2.25 \times 10^{-3}$ mM, Catalog # SUNBRIGHT PTE-200GS, NOF America Corporation, White Plains, N.Y.) and PEG$_{20kDa}$-[SH]$_4$ crosslinker (45 mg, 2.25×10$^{-3}$ mM, Catalog # SUNBRIGHT PTE-200SH, NOF America Corporation, White Plains, N.Y.) were added to the nanocarrier solution. The tube was tapped to obtain a clear solution. 0.1 mL of this solution was used for injection in each teat (~100 μg Dox equivalents per teat).

Intraductal Hydrogel Injection in Rats

Rat under anesthesia with isoflurane (AErrane, Catalog # NDC 10019-773-40, Baxter, Deerfield, Ill.) was placed under a surgical microscope as described in example 7A and hydrogel solution (0.1 ml) was injected into the third teat (counting from the head) using a 33 G needle as described in example 7A. The hydrogel solution was injected prior to the hydrogel setting and the process was repeated with two more rats.

Non-Invasive Hydrogel Detection in Rats

After the hydrogel administration, rats were immediately imaged (one at a time) on IVIS 100 optical imaging system (Xenogen Imaging Technologies, now part of Caliper Life Sciences, Hopkinton, Mass.). The system was set up as follows: Level: High; Em/Ex: GFP; Bin: HR (4); FOV 25; Aperture: f2; and Shutter: 1 s. The animals were then imaged at 1, 2, 3, 4, 5, 6, 7, 8, 9, 10, 11, 12, and 24 hours post administration. Fluorescent intensity of the injected area subtracted with that of uninjected distal area was used for nanocarrier quantitation in ducts.

Non-invasive detection of hydrogels with passively entrapped nanocarriers in rats breast duct are summarized in table 7B.

TABLE 8B

| Nanocarrier | Polymer | Crosslinker | Retention in ducts |
|---|---|---|---|
| PEG$_{20\,kDa}$-[CONH-RGDC(SH)-CONH-DOX]$_4$ | PEG$_{20\,kDa}$-[NHS]$_4$ | PEG$_{20\,kDa}$-[SH]$_4$ | 5.5 |
| PEG$_{40\,kDa}$-[CONH-RGDC(SH)-CONH-DOX]$_4$* | PEG$_{20\,kDa}$-[NHS]$_4$ | PEG$_{20\,kDa}$-[SH]$_4$ | 5.5 |

*The non-invasive detection studies were carried out as described in example 7B. Number of rats used was 3.

ABBREVIATIONS

ANPs: Aggregated nanogel particles
—CONH—: Amide bonds
DIPC: Diisopropylcarbodiimide
DLS: Dynamic light scattering
DMF: N, N-dimethylformamide
DOX: Doxorubicin hydrochloride, an anthracycline drug used in cancer chemotherapy
DYE: HiLyte Fluor™ 750 maleimide
DYE-ANPs: HiLyte750-labeled ANPs.
Eight-arm PEG-[SH]$_8$: Hexa-glycerine, octa-(thioethylene)poly(ethylene glycol) ether
Four-arm PEG-[NH$_2$]$_4$: Pentaerythritol, tetra-(aminopropyl)poly(ethylene glycol) ether
Four-arm PEG-[SH]$_4$: Pentaerythritol, tetra-(thioethylene)poly(ethylene glycol) ether
Four-arm PEG-[NHS]$_4$: Pentaerythritol, tetra-(succinimidylglutarate)poly(ethylene glycol) ether
h: Hours
HBVS: 1,6-hexane-bis-vinyl sulfone
HOBt: N-hydroxybenzotriazole
kDa: Kilo Daltons
Leu-Gly: Leucine-Glycine dipeptide
μL: Microliter
μm: Micron
MMP: 4-Methyl morpholine
min: Minutes
Na$_2$CO$_3$: Sodium carbonate
NHS: N-hydroxy succinimidyl ester (also called activated ester)
NOF: Name of the PEG supplier
NPs: Nanogel particles
PB: Phosphate buffer
PBS: Phosphate buffered saline
PEG: Poly(ethylene glycol) polymer
PyBOP: Benzotriazol-1-yl-oxytripyrrolidinophosphonium hexafluorophosphate
RGDC: Argine-Glycine-Aspartic acid-Cysteine; RGD tripeptide motif is recognized by integrin receptors overexpressed on tumor cell surfaces
—S—: Thioether bond
—S—CO—: Thioamide bond
SH: Thiol functional group
SPDP: N-Succinimidyl 3-(2-pyridyldithio)-propionate
—S—S—: Disulfide bond
—S—TP: Thiopyridine activated thiol group (also called activated thiol)
TEM: Transmission electron microscopy
temp: Temperature
TP: Thiopyridine
Tween 80: Polyethylene glycol sorbitan monooleate
Two-arm PEG-[NHS]$_2$: (Bis-succinimidylglutarate)poly(ethylene glycol) ether
Two-arm PEG[SH]$_2$: (Bis-thioethylene)poly(ethylene glycol) ether

What is claimed is:

1. A nanocarrier, comprising two doxorubicin molecules (Dox) coupled to at least one end of a linear polyalkylene oxide or a four-arm polyalkylene oxide by the linker Glu (Leu-Gly)$_2$ SEQ ID No: 1, wherein two or four Dox are coupled to said linear polyalkylene oxide and eight Dox are coupled to said four-arm polyalkylene oxide.

2. The nanocarrier of claim 1, wherein four Dox are coupled to said linear polyalkylene oxide and eight Dox are coupled to said four-arm polyalkylene oxide.

3. The nanocarrier of claim 1, wherein the aqueous solubility is at least about 100 mg/ml.

4. The nanocarrier of claim 1, wherein the four-arm polyalkylene oxide is four-arm polyethylene glycol.

5. The nanocarrier of claim 1, further comprising a targeting moiety.

6. The nanocarrier of claim 5, wherein the targeting moiety is peptide.

7. The nanocarrier of claim 5, wherein the targeting moiety is selected from the group consisting of an RGD peptide, a DV3 peptide, a LYP peptide, a membrane binding domain of IGFBP3, fMLF, mannose, transferrin ligand, and a monoclonal antibody.

* * * * *